(12) United States Patent
Chen et al.

(10) Patent No.: US 9,139,935 B2
(45) Date of Patent: Sep. 22, 2015

(54) ELECTROSTATIC-ASSISTED FIBER SPINNING METHOD AND PRODUCTION OF HIGHLY ALIGNED AND PACKED HOLLOW FIBER ASSEMBLY AND MEMBRANE

(75) Inventors: Chien-Chung Chen, Taipei (TW);
Jen-Chang Yang, Taipei (TW);
Jen-Chieh Lu, Taipei (TW);
Sheng-Yang Lee, Taipei (TW)

(73) Assignee: TAIPEI MEDICAL UNIVERSITY, Taipei (TW)

( * ) Notice: Subject to any disclaimer, the term of this patent is extended or adjusted under 35 U.S.C. 154(b) by 587 days.

(21) Appl. No.: 12/764,692

(22) Filed: Apr. 21, 2010

(65) Prior Publication Data
US 2011/0264235 A1    Oct. 27, 2011

(51) Int. Cl.
| | |
|---|---|
| *A61F 2/02* | (2006.01) |
| *D01D 5/00* | (2006.01) |
| *B01D 69/08* | (2006.01) |
| *D01D 5/24* | (2006.01) |
| *D01F 6/62* | (2006.01) |
| *D01F 8/14* | (2006.01) |
| *A61F 2/06* | (2013.01) |
| *B01D 61/14* | (2006.01) |

(52) U.S. Cl.
CPC .............. *D01D 5/0069* (2013.01); *B01D 69/08* (2013.01); *D01D 5/24* (2013.01); *D01F 6/625* (2013.01); *D01F 8/14* (2013.01); *A61F 2/06* (2013.01); *B01D 61/147* (2013.01); *B01D 2323/39* (2013.01); *Y10T 428/249924* (2015.04)

(58) Field of Classification Search
CPC .... A61F 2/06; A61K 31/4375; A61K 31/472; A61K 31/551; B01D 2323/39; B01D 61/147; B01D 69/08; D01D 5/0069; D01D 5/24; D01F 8/14; D01F 6/625; Y10T 428/249924
USPC ........ 424/402–404; 427/2.31; 442/37–41, 43, 442/46, 49–51; 606/151, 200, 213; 623/23.72–23.74
See application file for complete search history.

(56) References Cited

U.S. PATENT DOCUMENTS

| | | | |
|---|---|---|---|
| 4,911,846 A | * | 3/1990 | Akasu et al. .................. 210/645 |
| 7,575,707 B2 | | 8/2009 | Xia et al. |
| 2005/0238683 A1 | * | 10/2005 | Adhikari et al. .............. 424/423 |

FOREIGN PATENT DOCUMENTS

| | | | | |
|---|---|---|---|---|
| EP | 628596 A1 | * | 12/1994 | ............... C08K 7/14 |
| WO | 2005095684 | | 10/2005 | |

OTHER PUBLICATIONS

Sua Park et al., Apparatus for Preparing electrospun nanofibers: designing an electrospinning process for nanofiber fabrication, Polym Int 56:1361-1366, 2007.
A Theron et al., Electrostatic field-assisted alignment of electrospun nanofibres, Nanotechnology 12 (2001) 384-390.

(Continued)

*Primary Examiner* — Ashley Fishback
(74) *Attorney, Agent, or Firm* — WPAT, P.C.; Anthony King; Kay Yang

(57) ABSTRACT

The invention provides a highly aligned and closely packed hollow fiber assembly, wherein the assemblies of fibrous membrane has a width-to-fiber diameter ratio (W/d) larger than 10 and the orientation of the fibers is no larger than +/−10°. Also provided is an electrospinning process for the preparation of the fiber assembly of the invention and its applications.

19 Claims, 22 Drawing Sheets

(56) References Cited

OTHER PUBLICATIONS

P. Katta et al., Continuous Electrospinning of Aligned Polymer Nanofibers onto a Wire Drum Collector, Nano Lett., vol. 4, No. 11, 2004, 2215-2218.

Hao Fong et al., Generation of electrospun fibers of nylon 6 and nylon 6-montmorillonite nanocomposite, Polymer, 43 (3), 775-780, 2002.

Dan Li et al., Electrospinning of Polymeric and Ceramic Nanofibers as Uniaxially Aligned Arrays, Nano Lett., vol. 3, No. 8, 2003, 1167-1171.

J.M. Deitzel et al., Controlled deposition of electrospun poly(ethylene oxide) fibers, Polymer, vol. 42, 8163-8170, 2001.

Xing H. Li et al., A Simple Method for Controllable Preparation of Polymer Nanotubes via a Single Capillary Electrospinning, Langmuir 2007, 23, 10920-10923.

Yasmin Srivastava et al., Electrospinning hollow and core/sheath nanofibers using hydrodynamic fluid focusing, Microfluid Nanofluid (2008) 5:455-458.

Jiancheng Di et al., Fabrication of Zeolite Hollow Fibers by Coaxial Electrospinning, Chem. Mater., vol. 20, No. 11, 2008, 3543-3545.

* cited by examiner (a)

(b)

ELECTROSTATIC-ASSISTED FIBER SPINNING METHOD AND PRODUCTION OF HIGHLY ALIGNED AND PACKED HOLLOW FIBER ASSEMBLY AND MEMBRANE

FIELD OF THE INVENTION

The invention relates to an electrospun fiber assembly and an electrostatic-assisted fiber spinning method for the preparation of the fiber assembly. Particularly, the invention provides a highly aligned and closely packed fiber assembly, wherein at least 5 fibers are packed together and the orientation of the fibers is no larger than +/−5°, and its preparation and applications.

BACKGROUND OF THE INVENTION

There is a need for biomedical materials (preferably, biocompatible and biodegradable structural matrices) that facilitate tissue infiltration to repair/regenerate diseased or damaged tissue. Tissue engineering involves the development of a new generation of biomaterials capable of specific interactions with biological tissues to yield functional tissue equivalents. Most scaffolds can only introduce cells and/or signals after completion of the scaffold, due to the extreme conditions of the fabrication process, such as high or low temperature. The seeding of the cell in the inner part of a scaffold may be difficult, especially for larger objects with fine structural features. It would be very beneficial if cells could instead be introduced into the scaffold in situ. Furthermore, the addition of the chemical cues, such as growth factor, could be achieved in a controlled manner by fine tuning the degradation mechanism of biodegradable polymers such as collagen, polylactic acid and PCL.

It is known that nanotubes and nanofibers with core-sheath, hollow, or porous structures have many promising applications in a wide variety of technologies, including, for example, biomedical materials, scaffold and tissue regeneration and filtration. These fibers exhibit an especially advantageous combination of properties of being light-weight, flexible, permeable, strong and resilient in linear, two-dimensional and three-dimensional structures. In terms of biomedical application, there is great interest in devising a scaffold structure that mimics the tissue for better tissue regeneration. Highly aligned structure can be best represented by the structure of the nerve, vascular and some other tissues, or their parts.

Electrospinning is a process that relies on electric charges to deform a conical droplet of polymeric solution ejected from a nozzle tip into ultra-fine fibers. Electrospinning makes it relatively easy to spin continuous nanofibers from many different materials, including, but not limited to, polymers. Electrospinning provides a straightforward and practical way to produce fibers with diameters ranging from a few to about two-thousand nanometers. Electrospinning represents a versatile, low-cost method for producing micron- to nano-scale fibers in the form of either membrane or 3-D structure. An apparatus for preparing electrospun nanofibers is introduced in Polym Int 56:1361-1366, 2007. WO 2005095684 is directed to substantially continuous fibers which have a core-and-shell structure; however, these fibers are randomly arranged, not aligned and packed. Currently there are only limited reports of production of highly aligned electrospun fibers, either by collecting fibers with a rotating disc (A. Theron, E. Zussman and A. L. Yarin, "Electrostatic field-assisted alignment of electrospun nanofibres," Nanotechnology, Vol. 12, P 384-390, 2001), drum (P. Katta, M. Alessandro, R. D. Ramsier, and G. G. Chase, "Continuous Electrospinning of Aligned Polymer Nanofibers onto a Wire Drum Collector," Nano Lett., Vol. 4, No. 11, 2004) or frame (H. Fong, W-D. Liu, C-S. Wang, R A. Vaia, "Generation of electrospun fibers of nylon 6 and nylon 6-montmorillonite nanocomposite," Polymer, 43(3), P 775-780, 2002), or with a set of parallel conductive substrates (Dan Li, Yuliang Wang, and Younan Xia, "Electrospinning of Polymeric and Ceramic Nanofibers as Uniaxially Aligned Arrays," Nano Lett., Vol. 3, No. 8, 2003). Some degree of fiber orientation with the aid of the multiple-field technique has also been reported (J. M. Deitzel, J. Kleinmeyer, J. K. Hirvonen, Beck TNC., "Controlled deposition of electrospun poly(ethylene oxide) fibers," Polymer, Vol. 42, P 8163-8170, 2001). Moreover, U.S. Pat. No. 7,575,707 discloses a method for electrospinning nanofibers having a core-sheath, tubular, or composite structure.

However, the above references all have the disadvantage of limited alignment, which becomes even worse as the deposited fiber layers grow thicker. Also troublesome is the very limited production speed and/or small production quantity of electrospinning with needle type spinnerets, which makes it lack industrial value.

There are few reports on the preparation of nano/micro tube by electrospinning process. Li et al reported preparing nanotube via a single capilliary electrospinning (Li, X. H. S., Chang L. and Liu, Yi C., A Simple Method for Controllable Preparation of Polymer Nanotubes via a Single Capillary Electrospinning. Langmuir, 2007, 23: p. 10920-10923). Core/sheath, PPy/PVP and hollow PVP nanofibers were also prepared by Srivastava using hydrodynamic fluid focusing microchannel design (Srivastava, Y. R., C.; M.; Thorsen, T., Electrospinning hollow and core/sheath nanofibers using hydrodynamic fluid focusing; Microfluid Nanofluid, 2005, 5:p. 455-458). Di et al. prepared zeolite hollow fiber by calcinations of the as-spun fibers from coaxial electrospinning of the silicalite-1 nanoparticles in poly(vinyl pyrrolidone) (PVP)/ethanol solution to the outer shell and paraffin oil acted as the inner liquid (Di, J. C. C., H.Y., Wang, X. F., Zhao, Y, Yu, J. H. and Xu, R. R., Fabrication of Zeolite Hollow Fibers by Coaxial Electrospinning. Chem. Mater., 2008, 20(11): p. 3543-3545). However, none of them was able to prepare highly aligned and highly packed micro-tube. Accordingly, there is a need to develop structurally aligned and closely packed fibers.

SUMMARY OF THE INVENTION

One object of the invention is to provide a highly aligned and closely packed fiber assembly, wherein at least five (5) fibers are packed together to form a single layer and the orientation of the fibers is no larger than +/−5°.

Another object of the invention is to provide a method of preparing a fiber assembly of the invention by electro spinning a polymeric solution, comprising increasing the weight of jetted fiber by adjusting parameters of electrospinning so that the weight of the resulting fiber is least 40% of its original weight after the solvent in the solution vaporizes.

DETAILED DESCRIPTION OF THE INVENTION

Figure 1:
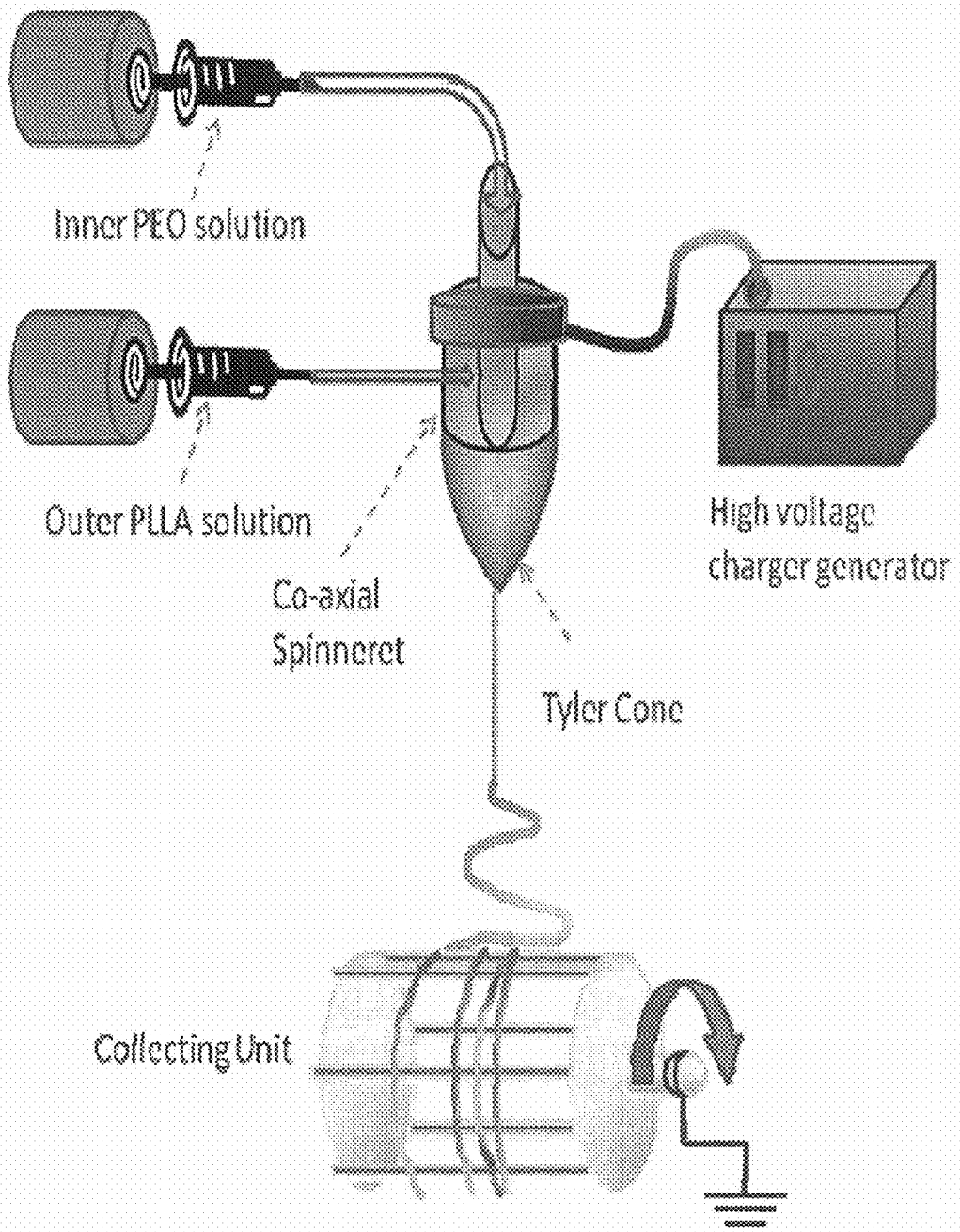
FIG. 1 shows a schematic diagram of an electrospinning of a coaxial electro spinning setup with a drum collecting unit, which is suitable for practicing the method of the invention.

The invention allows development of a highly aligned and closely packed fiber assembly which can be used in a medical device (such as scaffold and membrane for tissue regeneration) and micro-conduit.

Although many of the words, terms and titles employed herein are commonly used and conventionally understood within traditional medical and scientific contexts, summary descriptions and definitions of some terms and of particular names, designations, epithets or appellations are provided below. These descriptions and definitions are provided as an aid in recognizing and appreciating the true variety and range of applications intended for inclusion within the scope of the present methodology.

As used herein, the term "electrospinning" refers to a technology which produces nano-sized fibers referred to as electrospun fibers from a solution using interactions between fluid dynamics and charged surfaces. In general, formation of the electrospun fiber involves providing a solution to an orifice in a body in electric communication with a voltage source, wherein electric forces assist in forming fine fibers that are deposited on a surface that may be grounded or otherwise at a lower voltage than the body. In electrospinning, a polymeric solution or melt provided from one or more needles, slots or other orifices is charged to a high voltage relative to a collection grid. Electrical forces overcome surface tension and cause a fine jet of the polymeric solution or melt to move towards the grounded or oppositely charged collection grid.

As used herein, the term "polymer" refers to and generally includes, but is not limited to, homopolymers, copolymers, such as, for example, block, graft, random and alternating copolymers, terpolymers, etc. and blends and modifications thereof. Preferably, it can include, but are not limited to, polylactides, polylactic acids, polyolefins, polyacrylonitrile, polyurethane, polycarbonate, polycaprolactone, polyvinyl alcohol (PVA), cellulose, chitosan nylon (e.g., nylon 6, nylon 406, nylon 6-6, etc.), polystyrene, proteins, and the like, or combinations thereof. Unless otherwise specifically limited, the term "polymer" is intended to include all possible geometrical configurations of the material. These configurations include, but are not limited to, isotactic, syndiotactic and random symmetries. Suitable solvents for each polymer can be selected from solvents known to those skilled in the art, including, but not limited to, sulfuric acid, formic acid, chloroform, tetrahydrofuran, dimethyl formamide, water, acetone, and combinations thereof.

As used herein, the term "nano-sized fibers" or "nanofibers" refers to very small diameter fibers having an average diameter not greater than about 1500 nanometers (nm). Nanofibers are generally understood to have a fiber diameter range of about 10 to about 1500 nm, more specifically about 10 to about 1000 nm, more specifically still about 20 to about 500 nm, and most specifically about 20 to about 400 nm. Other exemplary ranges include about 50 to about 500 nm, about 100 to 500 nm, or about 40 to about 200 nm. In instances where particulates are present and heterogeneously distributed on nanofibers, the average diameter of a nanofiber can be measured using known techniques (e.g., image analysis tools coupled with electro microscopy), but excluding the portions of a fiber that are substantially enlarged by the presence of added particles relative to the particle free portions of the fiber.

As used herein, the term "oriented fibers" indicates that substantially all fibers in a specific structure or array are arranged parallel to each other in a longitudinal direction ("unidirectionally oriented") or in a well-defined three-dimensional network ("three-dimensionally oriented"). In other words, the fibers are not randomly spatially arranged with respect to each other. In most instances, the fibers described herein grow in a generally perpendicular direction relative to the supporting substrate surface and there is very minimal, if any, branching of individual fiber strands.

As used herein, the term "single layer of material" or "single-layered material" refers to a material composed of a single layer which can be variable in thickness.

As used herein, the term "plurality of layers" or "multi-layered material" refers to a "stack" of single-layered materials.

Highly Aligned and Closely Packed Fiber Assembly

In one aspect, the invention provides a highly aligned and closely packed fiber assembly, wherein at least five (5) fibers are packed together to form a single layer and the orientation of the fibers is no larger than +/−5°. According to the invention, the fibers can be hollow or solid. Preferably, the fibers are hollow.

The numbers of fibers packed together and the orientation angle of the fibers in the fiber assembly represent the degrees of packing and alignment, respectively. A larger fiber number means greater packing density, whereas a smaller orientation angle shows the degree of electrospun fiber alignment. In one embodiment, at least five (5) fibers in the fiber assembly are packed together; preferably, at least 20 fibers; more preferably, at least 50 fibers; and most preferably, at least 100 or 200 fibers are packed together. In further embodiments, the number of the fibers packed together in the fiber assembly ranges from 5 to 200, 20 to 200, 10 to 200, 20 to 200, 20 to 100, 50 to 200 or 50 to 100.

In another embodiment, the fiber orientation in the assembly is no larger than +/−5°; preferably, no larger than +/−4°; more preferably, no larger than +/−2°; most preferably, no larger than +/−1°. In one further embodiment, the fiber orientation in the assembly is about +/−1° to about +/−5°, and more preferably, about +/−1° to about +/−4°.

The length-to-diameter (outer) ratio (L/d) of fibers is another parameter of packing density of fibers. According to another embodiment of the invention, the L/d is larger than about 20. Preferably, the L/d is larger than about 100, more preferably, larger than about 1,000, and most preferably, larger than about 10,000. In one embodiment of the invention, the L/d is about 20 to about 10,000. Preferably, the ratio is about 20 to 1,000, and more preferably, about 20 to about 100.

The fibers in the fiber assembly prepared according to the invention are hollow. The fiber diameter is not an essential characteristic of the invention. The average inner diameter of the fibers in the assembly is about 1 to about 100 μm (micrometer). More preferably, the average diameter is about 10 to about 50 μm or about 15 to about 25 μm. Most preferably, the average diameter is about 20+/−2 μm. The average wall thickness of fibers is about 0.1 to about 10 μm. More preferably, the average wall thickness is about 1 to about 5 μm. Most preferably, the average wall thickness is about 3 μm.

According to the invention, any suitable polymer can be used in the preparation of the fibers of the invention. Examples of polymers include, but are not limited to, ethylene oxide, polyethylene oxide (PEO), ethylene glycol, polyethylene glycol (PEG), poly(lactic acid) (PLA), poly(glycolic acid) (PGA), poly(ethylene oxide) (PEO), nylon, polyesters, polyamides, poly(amic acids), polyimides, polyethers, polyketones, polyurethanes, polycaprolactones, polyacrylonitriles, polyaramides, conjugated polymers such as the electroluminescent polymer, poly(2-methoxy, 5 ethyl (2' hexyloxy) para-phenylene vinylene) (MEH-PPV), polyphenylenevinylenes, polyarylene-vinylenes, polythienolene-vinylenes, polypyrrolo-vinylenes, polyheteroarylene-vinylenes, polyanilines, polyphenylenes, polyarylenes, polythiophenes, polypyrroles, polyheteroarylenes, polyphenylene-ethynylenes, polyarylene-ethynylenes, polythienoethynylenes, polyheteroarylene-ethynylenes, and mixtures thereof.

In an embodiment of the invention useful for preparing hollow fibers having utility in medical applications, the polymer is a biodegradable and/or bioabsorbable polymer which contains a monomer selected from the group consisting of a glycolid, lactide, dioxanone, caprolactone and trimethylene carbonate. The phrase "contains a monomer" is intended to refer to a polymer which is produced from the specified monomer(s) or contains the specified monomeric unit(s). The polymer can be a homopolymer, random or block co-polymer or heteropolymer containing any combination of these monomers. The material can be a random copolymer, block copolymer or blend of homopolymers, copolymers, and/or heteropolymers that contains these monomers.

In one embodiment, the biodegradable and/or bioabsorbable polymer contains bioabsorbable and biodegradable linear aliphatic polyesters such as polyglycolide (PGA) and its random copolymer poly(glycolide-co-lactide) (PGA-co-PLA). The Food and Drug Administration has approved these polymers for use in surgical applications, including medical sutures and scaffold for tissue building. An advantage of these synthetic absorbable materials is their degradability by simple hydrolysis of the ester backbone in aqueous environments, such as body fluids. The degradation products are ultimately metabolized to carbon dioxide and water or can be excreted via the kidney. These polymers are very different from cellulose-based materials, which cannot be absorbed by the body.

Other examples of suitable biocompatible polymers are polyhydroxyalkyl methacrylates including ethylmethacrylate, and hydrogels such as polyvinylpyrrolidone, polyacrylamides, etc. Other suitable bioabsorbable materials are biopolymers which include collagen, gelatin, alginic acid, chitin, chitosan, fibrin, hyaluronic acid, dextran and polyamino acids. Any combination, copolymer, polymer or blend thereof of the above examples is contemplated for use according to the present invention. Such bioabsorbable materials may be prepared by known methods.

Particularly useful biodegradable polymers include polylactides, poly-glycolides, polycarprolactone, polydioxane and their random and block copolymers. Examples of specific polymers include poly D,L-lactide, polylactide-co-glycolide and polylactide-co-glycolide.

In another embodiment, the fibers of the fiber assembly of the invention have a core-shell structure. Preferably, the shell layer is composed of poly-L-lactic acid, poly(lactic-co-glycolic acid) or the mixture thereof and the core layer is composed of polyethylene glycol, polyethylene oxide, PF127 or the mixture containing two or more the above-mentioned components.

The invention provides "epitaxial growth"-like highly aligned and closely packed fibers. According to the invention, the fibers of the invention are oriented fibers. In one embodiment of the invention, more than 98% of fibers have an orientation angle no larger than +/−10° and more than 80% of fibers have an orientation angle ranging from 0 to +/−2°.

Production of Highly Aligned and Closely Packed Hollow Fiber Assembly

The fiber assembly of the invention can be produced by electrostatic assisted fiber spinning, including but not limited to wet spinning, dry spinning, electrospinning, etc. Preferably, the fiber assembly of the invention is produced by electrospinning. More preferably, the fibers are formed by use of a two-fluid electrospinneret.

In another aspect, the invention provides a method of preparing a fiber assembly of the invention by electrospinning a polymeric solution, comprising increasing the weight of jetted fiber by adjusting parameters of electrospinning so that the weight of the resulting fiber is at least 40% of its original weight after the solvent in the solution vaporizes. Preferably, the weight of the resulting fiber is at least 50% of its original weight after the solvent in the solution vaporizes. More preferably, the weight of the resulting fiber is 40% to 95% of its original weight after the solvent in the solution vaporizes. More preferably, the weight of the resulting fiber is 40% to 95%, 40% to 90%, 45% to 90%, 50% to 90%, 40% to 80% or 50% to 80% of its original weight after the solvent in the solution vaporizes. Preferably, the method of the invention is characterized by coaxial electrospinning a first polymeric solution as a shell (shell solution) around a second fiber solution as a core (core solution).

According to the invention, the weight of produced fibers can be controlled by mainly adjusting the flow rate and concentration of the solution. Other parameters can be used to co-control the weight of produced fibers. The other parameters include, but not limited to, voltage of electrospinning, the species of solvent in the solution, and the distance between the collector and spinneret. Persons skilled in the art can select and/or combine different parameters to achieve the purpose that the weight of the resulting fiber is 40% to 95% of its original weight after the solvent in the solution vaporizes.

It is known in the art that, in the electrospinning process, the formation of the electrospun fibers can be divided into three stages (1) Taylor cone (2) stable jet and (3) instable jet stage (Polym Int 56:1361-1366, 2007). At the first stage, electrical force is balanced with the solution viscosity and surface tension to form the Taylor cone. When electrical force is larger than surface tension of the solution, the solution begins to be pulled out of the Taylor cone and fly toward the grounded target. At the first part of jet flying phenomenon, the fibers possess initial inertial force and fly toward the direction of the predetermined electrical field. However, as the solvent vaporizes, the weight of the jet becomes smaller, while the charge on the fibers surface becomes larger. Not only the normal force act upon the jet fiber but also forces with different directions cause the side motion of the jet. Thus, the jetted fiber enters the instable stage. The swings of these fibers become larger and wider. When the jetted fibers are finally collected on the ground target, they are all random with no directional preference, as in most cases of electro spinning. The invention solves these problems. To obtain electrospun fibers with greatest alignment, it is important to collect these electrospun fibers before they enter the instable stage. The invention unexpectedly found that with the composition and electrospinning method of the invention, the jetted fiber can keep most of the original weight to extend its stable stage and is collected before entering the instable stage one fiber after another, i.e. in an "epitaxial growth"-like way.

In one embodiment of the method of the invention, coaxial electrospinning is used to electrospin a first polymeric solution as a shell and around a second fiber solution as a core. Through this process, polymeric solutions are delivered through a co-axial spinneret. In an embodiment, one solution is composed of organic solvent with a high vaporization rate (preferably, dichloromethane (DCM)) as the outer shell layer, while the other can be non-organic solvent, such as water, delivered through the inner core. After exiting the spinneret, Taylor cone is formed by applying voltage. With the increase of voltage, the solution starts jetting toward the grounded collector. During the early stage of the jet, as in most of the electrospinning process, the solvent of the outer layer vaporizes quickly, leaving a solidified skin of the polymer. However, the inner layer solvent has no chance to vaporize and is contained inside the jetted fibers. Under such circumstances, the weight of the fiber is kept at 50 or 60% of its original weight and the initial inertial force is still the dominated factor, keeping the fiber moving stably on its original track. With aid of a rotating drum-like collector, these fibers are collected at the same spot, which makes them overlap with each other in the rotating direction. This is very similar to the epitaxial growth of some semiconducting materials, such as GaAs/AlAs, CdSe/CdS, GaN and ZnO. At the very end the inner solution is washed away, leaving the highly packed and aligned hollow fibers.

For example, the concentration of the shell solution ranges from 6% to 25% (w/v). Preferably, the concentration of the first solution ranges from 13% to 20% (w/v), more preferably, 13% to 19% (w/v), and most preferably, 15% to 19%. Preferably, the first and second solutions contain one or more polymers, preferably, biodegradable polymers.

In a further embodiment, the flow rate of the core solution is 2 to 20 ml/hr, preferably, 4 to 12 ml/hr.

According to the invention, the hollow fibers are formed by using a suitable solvent to wash out the core. For example, aqueous solvents are used to remove the water soluble polymer components, while organic solvents are used to remove water insoluble polymer components.

In FIG. 1, a schematic diagram of an coaxial electrospinning setup with a drum collecting unit. The electrospinning setup suitable for practicing the methods described herein is shown. The electrospinning setup includes a coaxial spinneret having an inner tube and an outer tube. The core solution flows into the inner tube and the shell solution 6 flows into the outer tube. A voltage charger generator is connected to the coaxial spinneret to prove voltage. The Tayler cone is also shown in the figure.

According to the invention, the voltage applied is no less than 10 kV to induce a jet stream of said first and second solutions to travel from the coaxial spinneret to the collector with the rotating speed of 50 to 60 m/min to form a fiber assembly. The core solution and shell solution flow rates are comparable for both systems. The solutions' properties (viscosity, conductivity, and surface tension) need to be within the general ranges specified above. All solutions are polymer in solvent. Specific processing conditions are detailed in the Examples. Each of the solutions was delivered to a two-fluid coxial electrospinneret as a core or shell fluid at appropriate flow rates. The voltage applied to the spinneret would not pull the fluids too fast or too slow at the nozzle. The resulting fibers were examined by taking fiber images using electron microscopes.

Applications

The highly aligned and closely packed fiber assembly of the invention can be used in various applications. For example, solid fiber assembly can be used as solid support or isolating material. Hollow fiber assembly can be used in biotechnology. The highly aligned and closely packed hollow fiber assembly of the invention can be prepared in various shapes for different applications including medical tissue engineering (such as scaffold, nerve guide conduit and vascular tube) and filtration unit. For example, the highly aligned and closely packed hollow fiber assembly of the invention can be rolled into a tube with a tube-in-tube structure that can be used as nerve guide conduit. In addition, the fiber assemblies can be stacked to form a filtration membrane.

In one embodiment, the highly aligned and closely packed hollow fiber assembly of this invention used as medical device/scaffold can be in situ seeded with cells, whereby the cells are suspended in the scaffold and exposed to the appropriate molecular cues in 3-D. These cell-seeded hollow fiber assemblies are useful in tissue replacement protocols. According to this embodiment, tissue can be reconstituted in vitro and then implanted into a host in need thereof. Useful cells include nerve cells, epithelial cells, endothelial cells, fibroblasts, myoblasts, chondroblasts, osteoblasts, and neural stem cells. Other cells that may be useful in the methods and fiber assemblies of this invention include, Schwann cells (WO 92/03536), astrocytes, oligodendrocytes and their precursors, adrenal chromaffin cells, and the like.

In another embodiment, the fiber assemblies of the invention can form porous membrane used as a micro-filtration membrane for filtration, more particularly a hollow fiber-form porous water filtration membrane.

EXAMPLE

Example 1

Electrospinning Process

Materials used in fabrication of the hollow fiber assembly were poly-L-lactic acid (PLLA; Mw=140000 Da, Japan), poly-ethylene glycol (PEG; Mw=35000 Da, Sigma-Aldrich), poly-ethylene oxide (PEO; Mw=900000 Da, Sigma-Aldrich), and solvent of Dichloromethane (DCM; Mallinckrodt, USA) and N,N-Dimethyl formamide, were purchased from Sigma-Aldrich, Inc. (St. Louis, Mo.). These polymers and solvent for electrospinning were used as received without further purification.

The outer shell of PLLA solution varied from 12% (wt/vol) to 20%(wt/vol)(12%, 15%, 17%, and 20%) in Dichloromethane (DCM) and N,N-Dimethyl formamide (DMF) at ratio of 9:1. Aqueous PEG/PEO (weight ratio=1:1) solution was obtained by dissolution in 10% (wt/vol) of double distilled water. The PEG/PEO solution was delivered to the inner core. The electrospinning parameters for obtaining the PLLA/PEG-PEO shell-core fibers were as follows: 6 cm gap distance, 14.6 kV applied voltage, 5 mL/h inner flow rate, 6 mL/h outer flow rate, 58.5 m/s collecting rate, a relative humidity of about 68%, and at room temperature (about 25° C.).

After using a rotating collector at a rate 58.5 m/s, the PLLA/PEG-PEO shell-core fibers were collected as a highly aligned fibrous membrane. The higher the concentration of PLLA, the higher the alignment. The PLLA/PEG-PEO shell-core fibers were placed in double distilled water for 24 hr after being cut into slices of membranes, and the inner core PEO-PEG fibers was dissolved, then the highly electrospun hollow fiber was fabricated.

Example 2

Preparation of Fiber Assembly of the Invention

Figure 2:
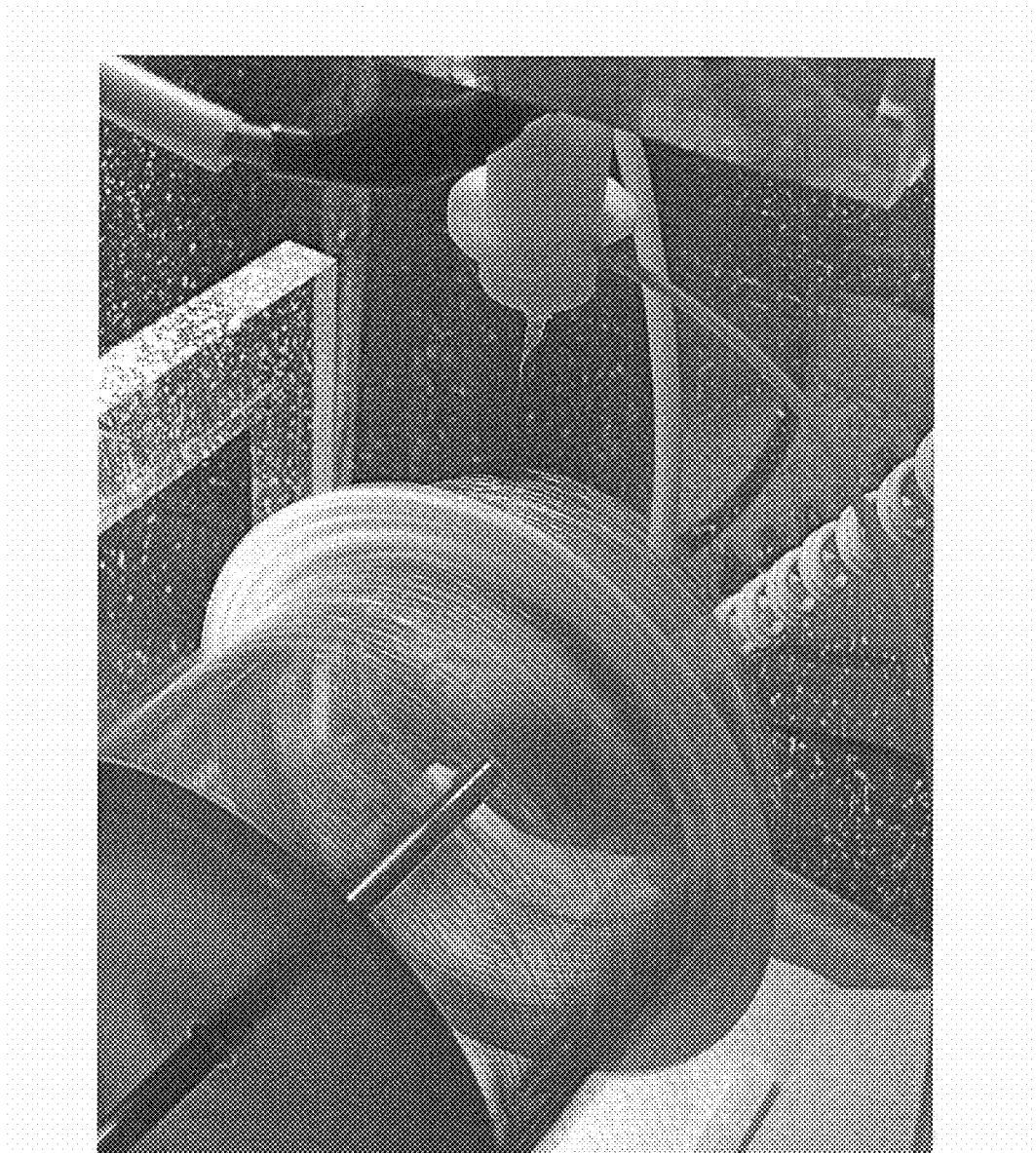
FIG. 2 shows the physical appearance of "standing" fibers of the invention collected on the present rotating collector.
Figure 3:
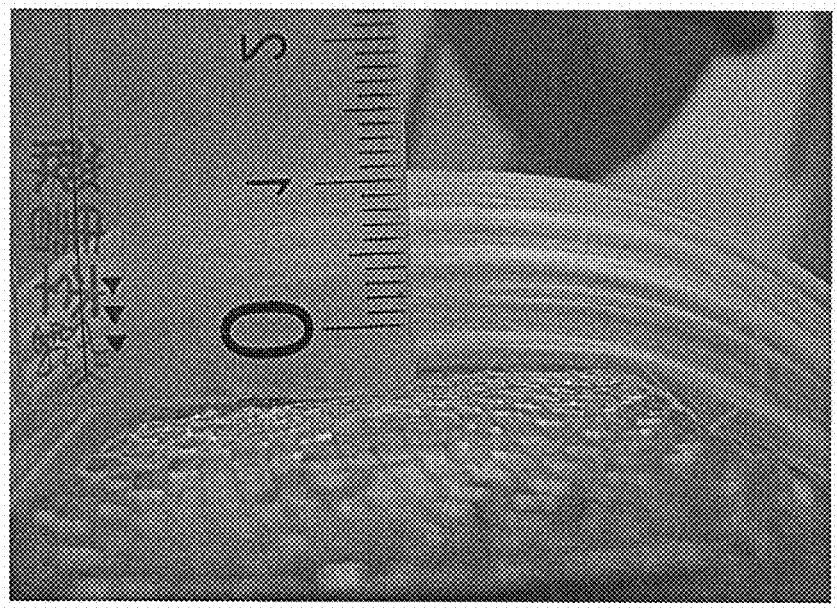
FIG. 3 shows the (a) side view and (b) top view of the collected stood-up PLLA fibrous membrane.
Figure 3:
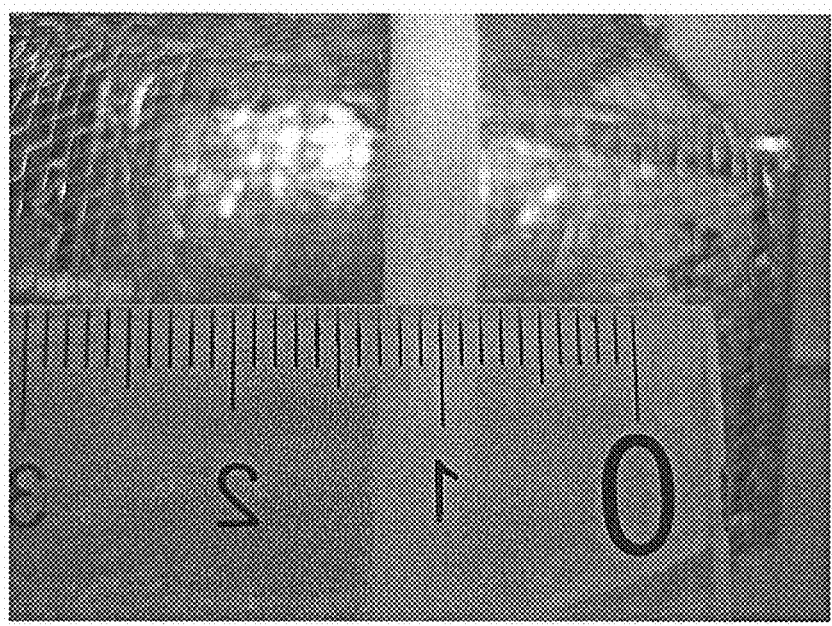
Figure 4:
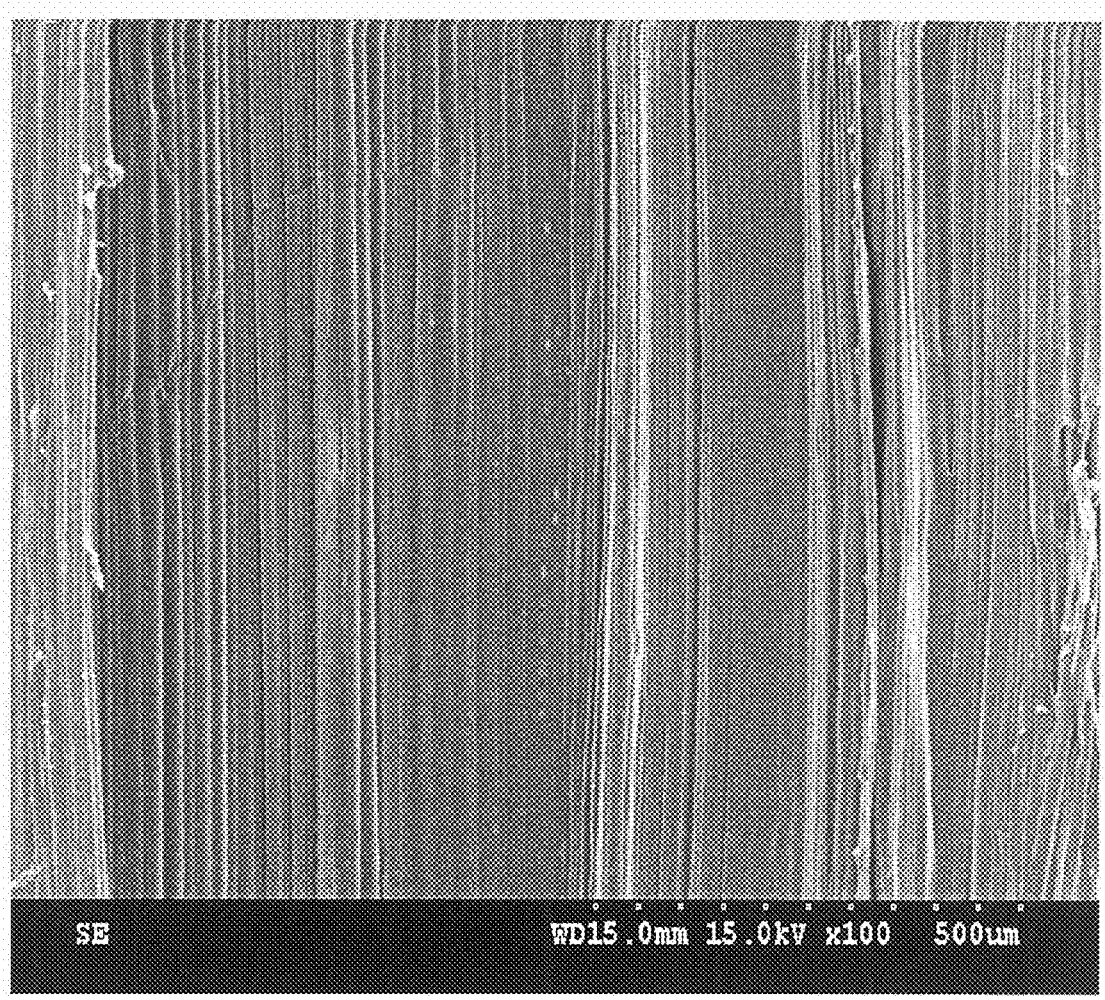
FIG. 4 shows the large area of highly aligned and closely packed hollow PLLA hollow fibers.
Figure 5:
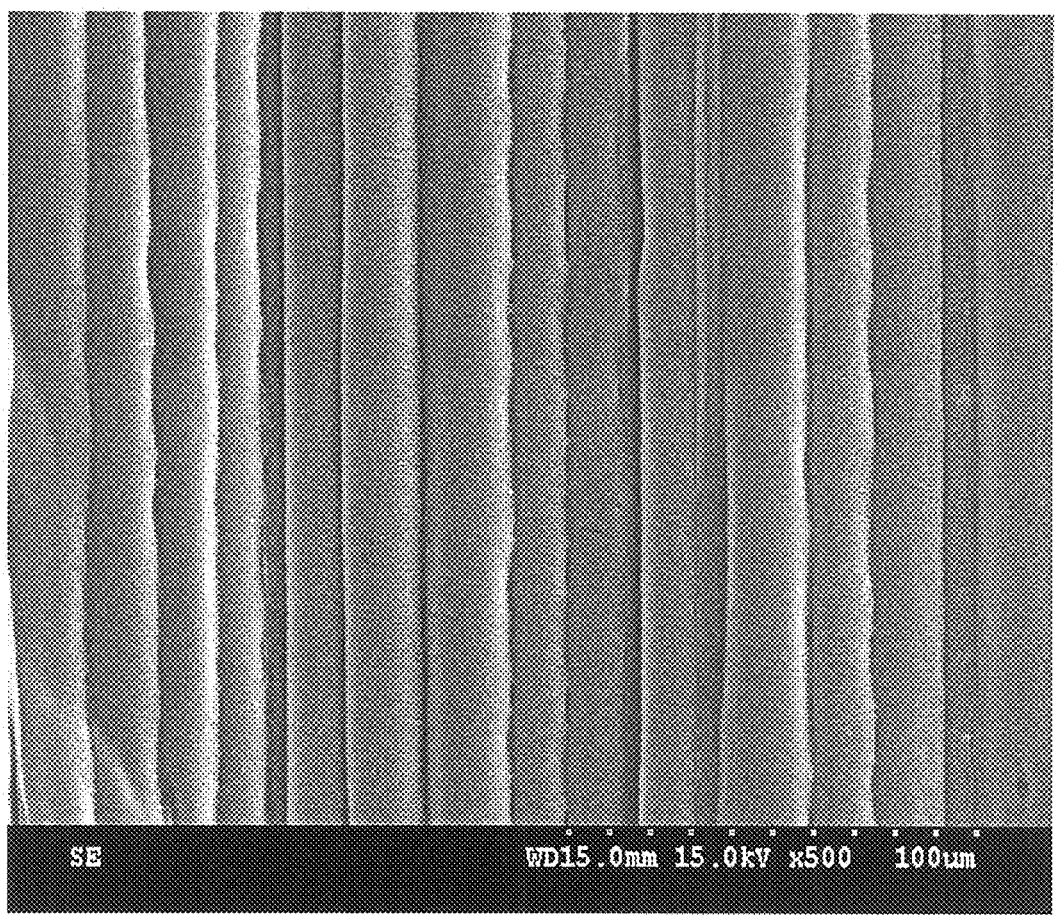
FIG. 5 shows the highly aligned and closely packed hollow PLLA fibers (detail).
Figure 6:
FIG. 6 shows SEM photography of the highly aligned and closely packed PLLA hollow fibers (showing both cross section and surface).
Figure 7:
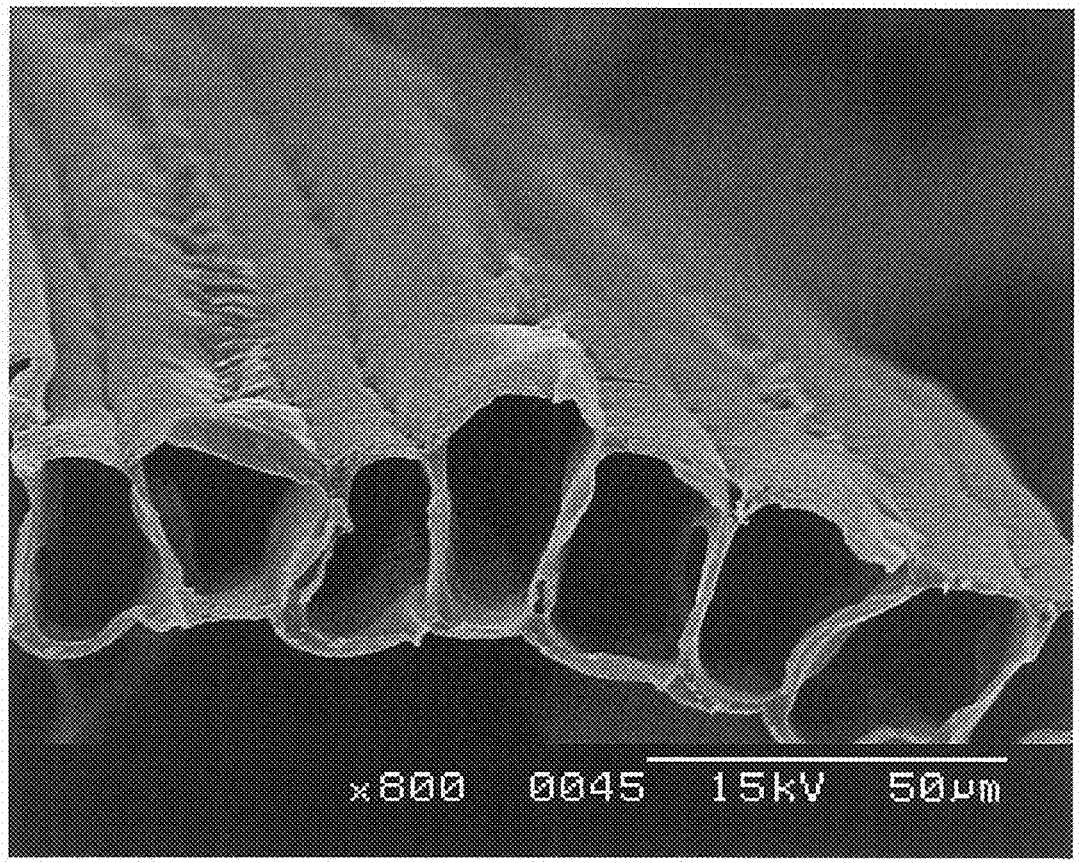
FIG. 7 shows the highly aligned and closely packed electrospun PLLA hollow fibers (cross section in detail).
Figure 8:
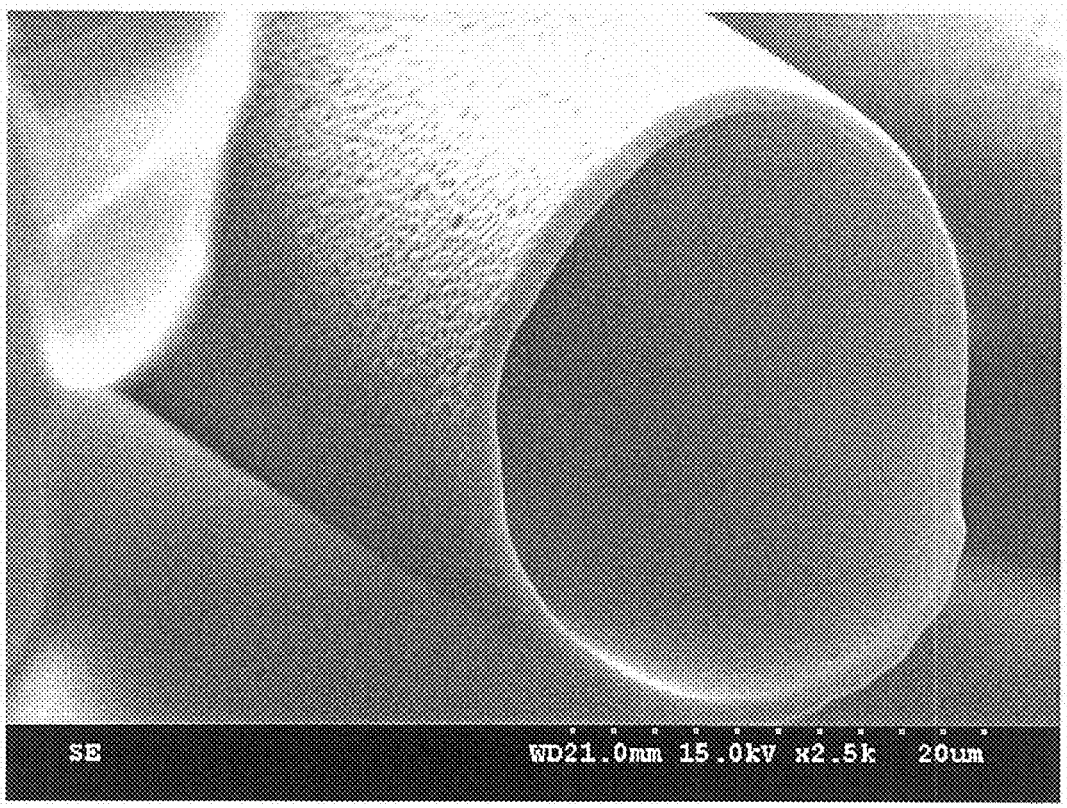
FIG. 8 shows SEM photography of cross view of electrospun PLLA hollow fiber with solid wall.

A coaxial spinneret connected to high voltage power source was used as the material dispenser. Two polymeric solutions (PLLA, 17%, wt/vol., in dichloromethane and PEG/PEO 50/50, 10%, wt/vol. in d. d. water) were pumped to the outer tube and inner tube of the coaxial spinneret individually by syringe pumps at rate of 5 ml/hr and 4 ml/hr, respectively. After 14.6 kV of high voltage was applied, the polymeric solutions were ejected from the spinneret and the electrospun fibers were collected by a rotating metal frame 6 cm apart. The collecting frame was rotated at the speed of 58.5 m/s. The operation was carried out at the temperature of 25° C. with a relative humidity of 68%. The resulting fibers collected on the metal frame were shown in FIG. 2. In contrast with the usually seen random spreading mode of the collected electrospun fibers, these fibers were collected on a very narrow range. As the operating time grew longer, these fibers piled up on this very narrow range and finally stood up and perpendicular to the surface of the collecting unit, as seen in FIG. 3. The fibers were then washed by water to remove the water soluble component so that a hollow structure was formed. After examining with scanning electronic microscopy, a sheet of large area, aligned conduits were observed, as shown in FIG. 4. What was striking was that these fibers were perfectly attached in a way that had never been seen before, as shown in FIG. 5. They were attached and aligned one by one to form a sheet with single-fiber thickness. The height of the standing membrane can reach 2 to 3 cm (1 cm in this case) in less than twenty minutes, with only 3 to 4 millimeter in the deposition width, as shown in FIGS. 4 and 5. The cross-section views showed that the fibers were closely packed one by one while still having the integrity of the hollow structure, as shown in FIGS. 6 and 7. Such perfectness in electrospun fiber alignment had never been reported in previous research. The dimension of these fibers was determined by image analysis software, ImageJ. It was found these hollow fibers had an average inner diameter of 19±1.5 micron, with the wall thickness of few microns. The wall of the hollow fiber was solid, as shown in FIG. 8.

Example 3

Preparation of Fiber Assembly of the Invention

Figure 9:
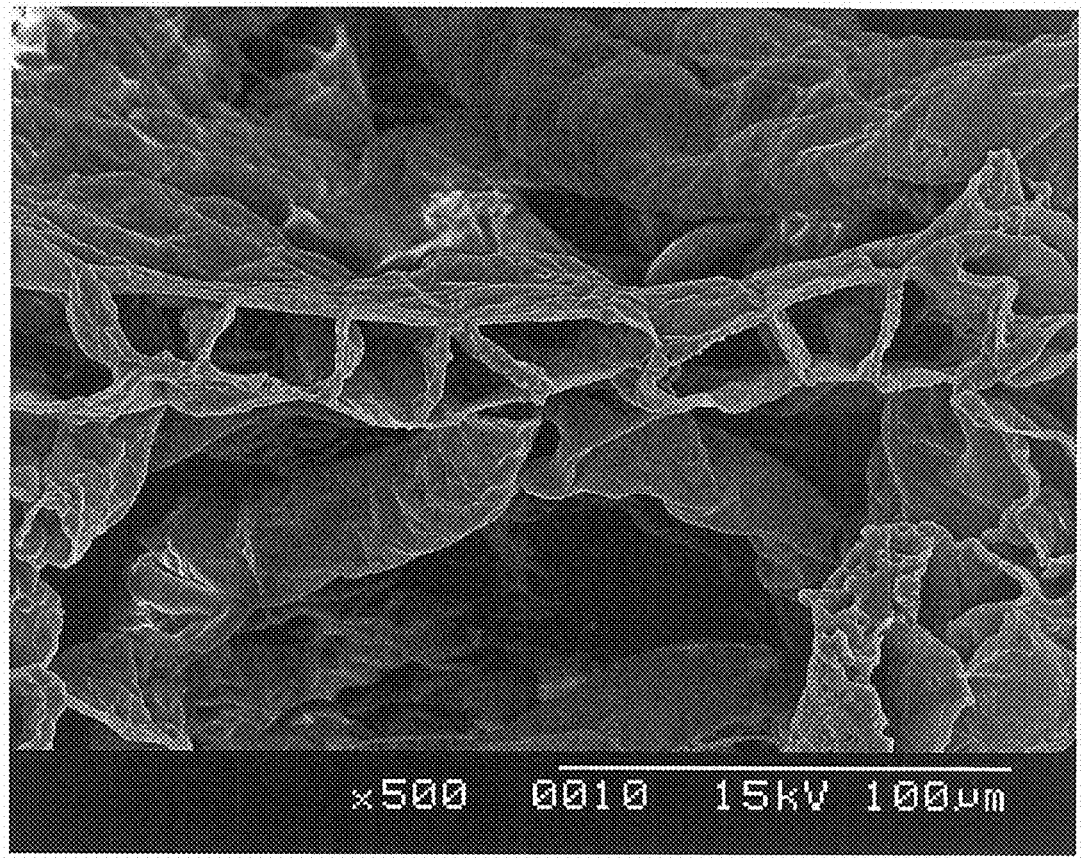
FIG. 9 shows SEM photography of cross view of electrospun PLGA hollow fibers.

A coaxial spinneret connected to high voltage power source was used as the material dispenser. Two polymeric solutions (PLGA, 17% wt/vol in dichloromethane and PEG/PEO, 10% wt/vol in d. d. water) were pumped to the outer tube and inner tube individually by syringe pumps at rate of 5 ml/hr and 4 ml/hr, respectively. After 14.6 kV of high voltage was applied, the polymeric solutions were ejected from the spinneret and the electrospun fibers were collected by a rotating metal frame 6 cm apart. The collecting frame was rotated at the speed of 58.5 m/s. The operation was carried out at the temperature of 25° C. with a relative humidity of 68%. The electrospun fibers were investigated by SEM, as shown in FIG. 9.

Example 4

Preparation of Fiber Assembly of the Invention

Figure 10:
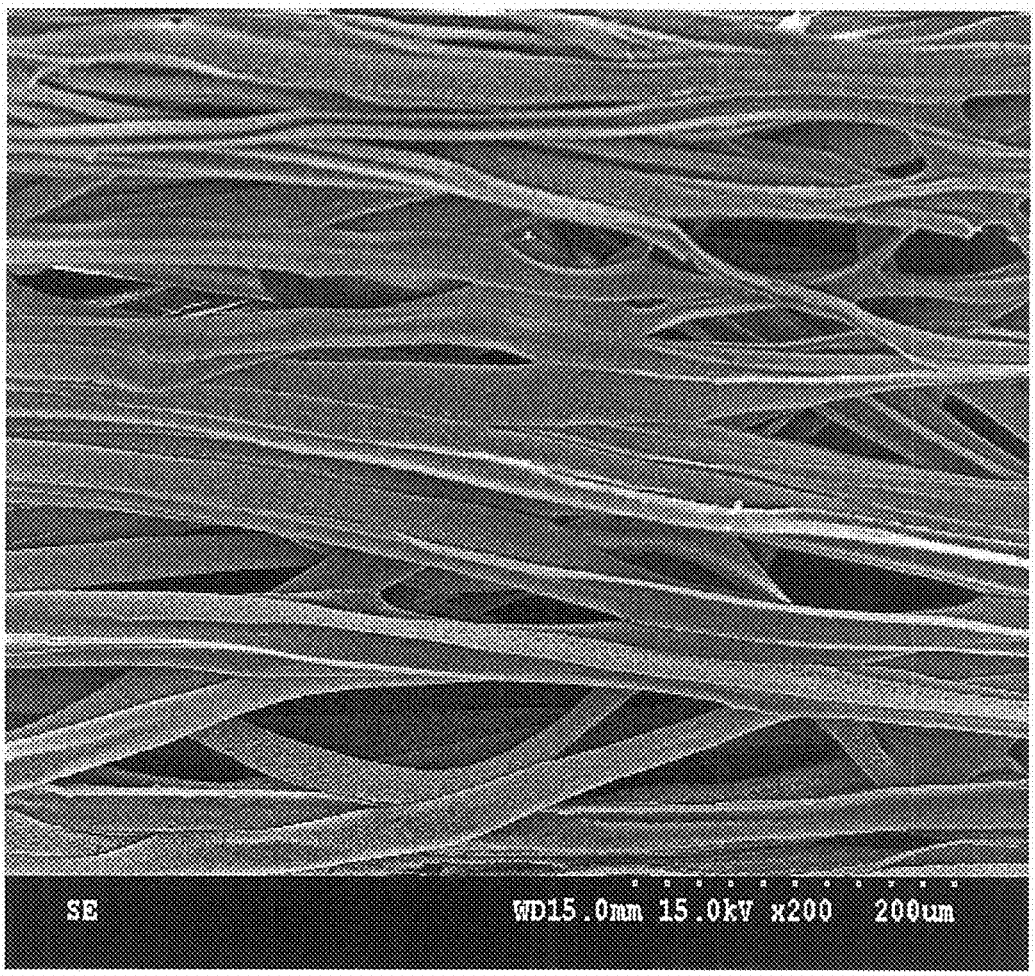
FIG. 10 shows SEM photography of electrospun PLLA hollow fiber with porous wall (top view).
Figure 11:
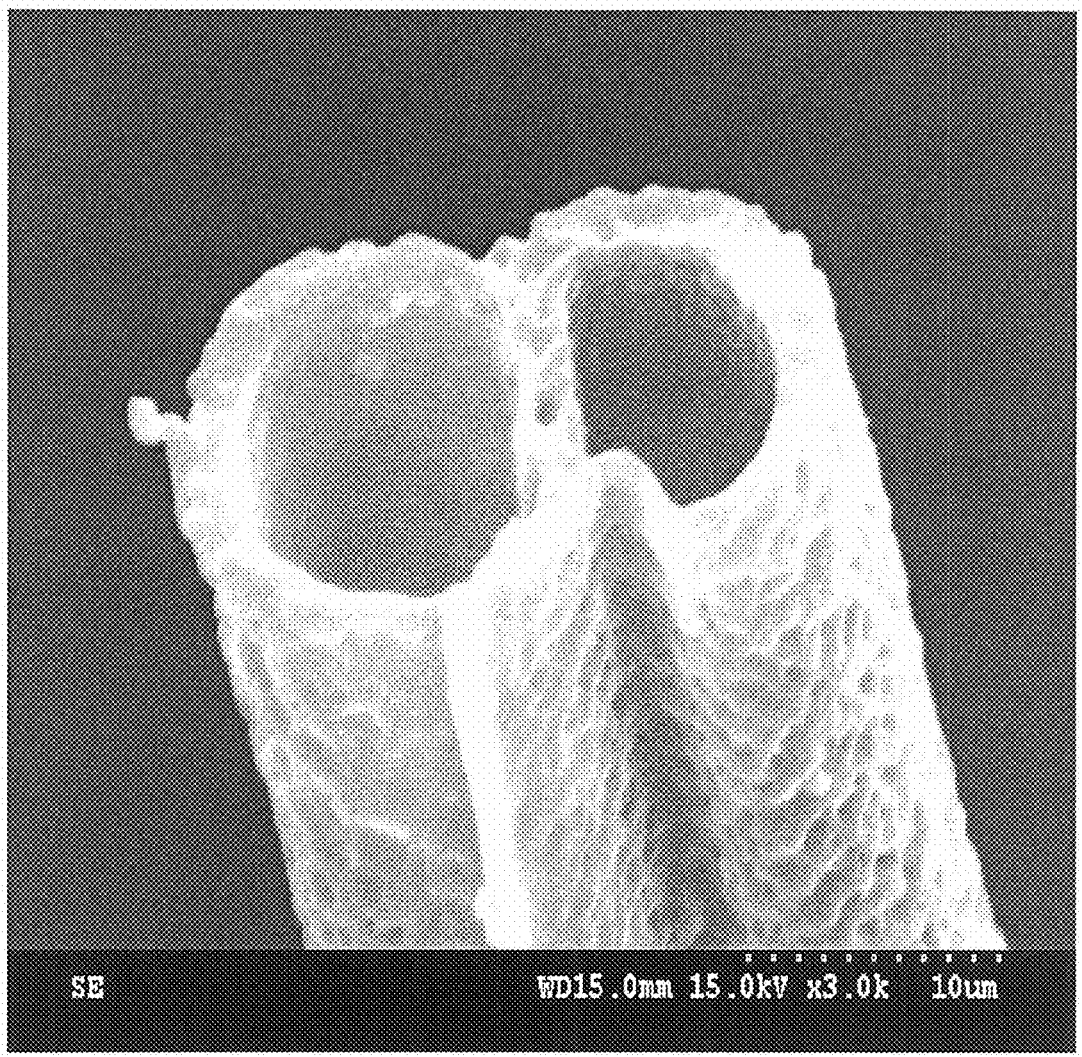
FIG. 11 shows SEM photography of electrospun PLLA fibers hollow with porous wall (cross-section view).
Figure 12:
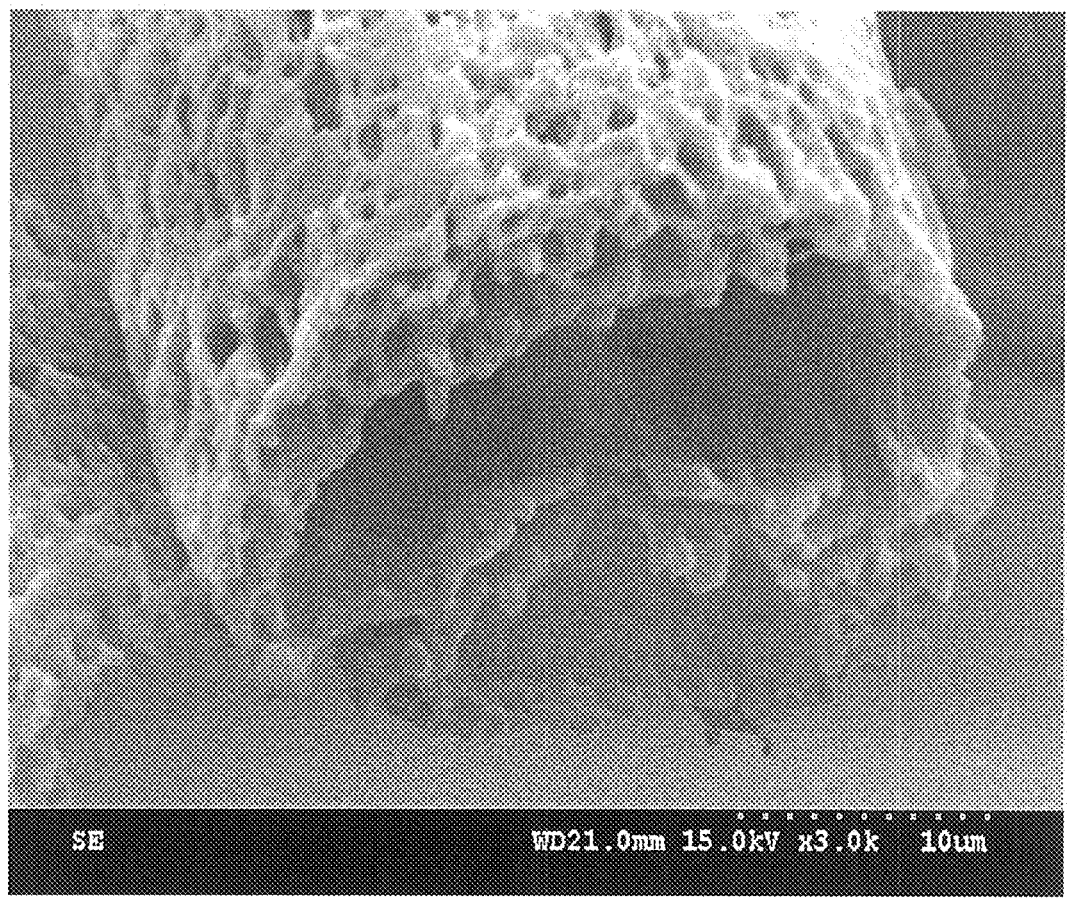
FIG. 12 shows SEM photography of electrospun PLLA hollow fiber with porous wall (detail).
Figure 13:
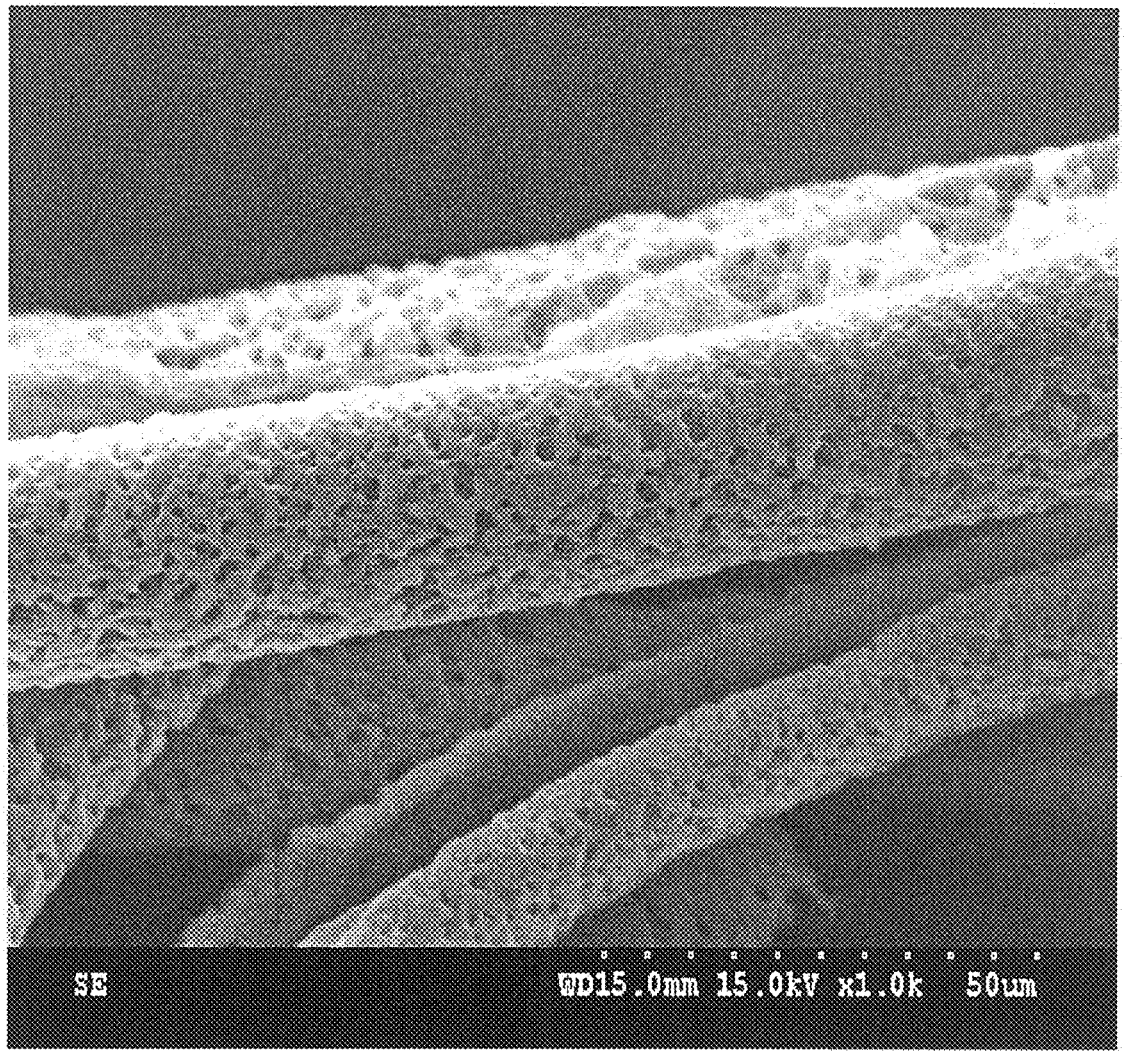
FIG. 13 shows SEM photography of electrospun PLLA hollow fiber with porous wall.

A coaxial spinneret connected to high voltage power source was used as the material dispenser. Two polymeric solutions (PLLA/PF127 "60/40 weight ratio", 17 wt % in DCM/DMF:9/1, and PEG/PEO:50/50, 10 wt % in d. d. water) were pumped individually by syringe pump at rate of 5 ml/hr and 4 ml/hr, respectively. After 14.6 kV of high voltage was applied, the polymeric solutions were ejected from the spinneret and the electrospun fibers were collected by a rotating metal frame 10 cm apart. The collecting frame was rotated at the speed of 58.5 m/s. The operation was carried out at the temperature of 25° C. with a relative humidity of 68%. After washing by d. d. water to remove water soluble components, the resulting thin film revealed not only hollow fibers but also a porous wall structure, as shown in FIG. 10. High orientation was achieved as shown in FIG. 11; however, it was not standing out as in the previous case. The diameter of these hollow fibers was in the range of tens of micron, with a wall thickness of a few microns. The porous wall structure was characterized by ImageJ software and the pore size was found to be in the range of sub-micron to a few microns. Preliminary permeation test confirmed the continuity of the pore within the wall. It was also proved that these porous hollow fibers could permeate liquid easily. FIGS. 12 and 13 are the SEMs of the electrospun fibers obtained from similar composition with the same operation parameters.

Example 5

Figure 14:
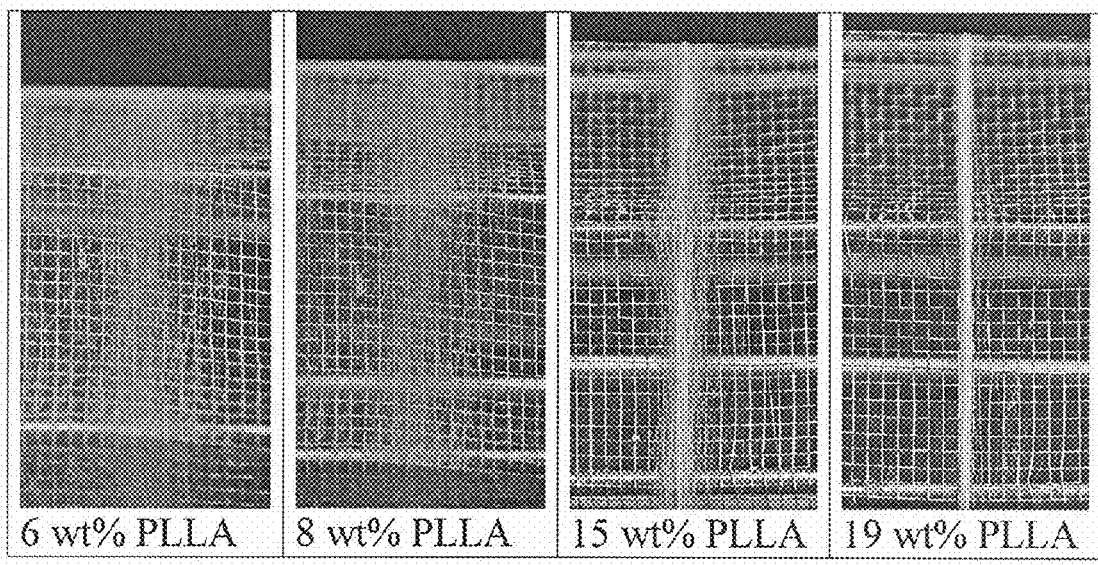
FIG. 14 shows the physical appearance of the collected electrospun PLLA hollow fibers prepared from different concentrations: (a) 6 wt % (b) 8 wt % (c) 15 wt % and (d) 19 wt %.
Figure 15:
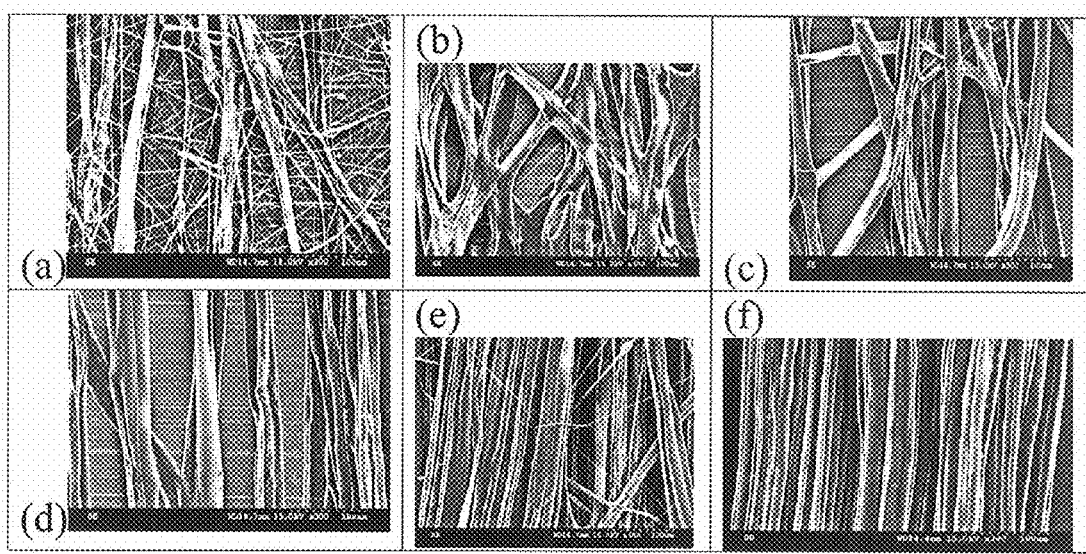
FIG. 15 shows the SEM images of PLLA hollow fibrous membranes prepared from different concentrations: (a) 8 wt % (b) 12 wt % (c) 15 wt % (d) 16 wt % (e) 17 wt % and (f) 19 wt %, at magnifications of 300×. Samples were collected in a 20-second period.
Figure 16:
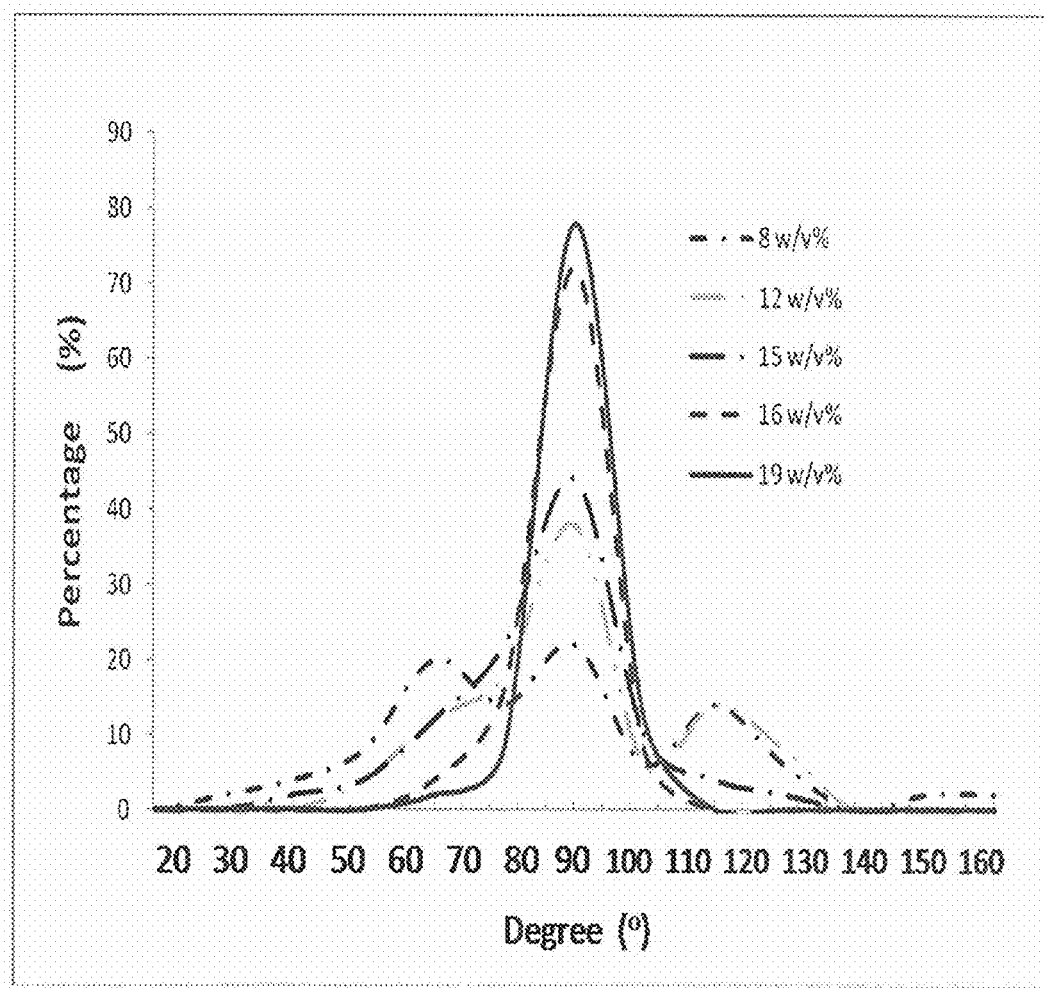
FIG. 16 shows the fiber alignment of PLLA hollow fibrous membranes prepared from different concentrations.

Preparation of Fiber Assembly of the Invention Using Polymeric Solutions of Various Concentrations The materials and methods were similar to those of Example 1 and only the concentration of PLLA solutions was changed. By using the shell PLLA solution of concentrations of 6, 8, 10, 15, 17 and 19 wt % of PLLA, it was observed that the collected fibers assembly scattered around the surface of the collecting drum when the solution was of lower concentration of 6 to 10 wt %. At higher concentrations, 15% to 16%, these fibers began to concentrate to a very narrow point and finally stood up when flow rate ratio reached 17% and 19%, as shown in FIG. 14. FIG. 15 shows the SEM images of PLLA hollow fibrous membranes prepared from different concentrations: (a) 8 wt % (b) 12 wt % (c) 15 wt % (d) 16 wt % (e) 17 wt % and (f) 19 wt %. With the increase in concentration, the fibers exhibit better alignment and tighter packing. The PLLA electrospun hollow fiber assembly has the highest alignment with concentration of 19 wt %, as shown in FIG. 16.

Example 6

Figure 17:
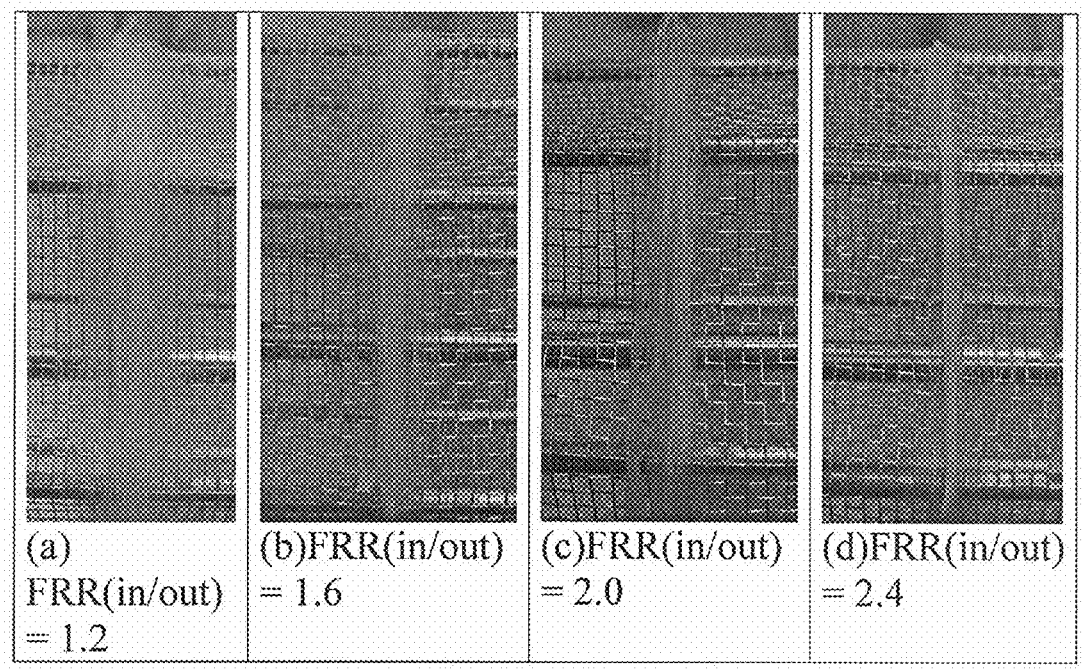
FIG. 17 shows the physical appearance of the collected electrospun PLLA hollow fibers prepared from different flow rate ratios: (a) 1.2 ml/hr (b) 1.6 ml/hr (c) 2.0 ml/hr and (d) 2.4 ml/hr.
Figure 18:
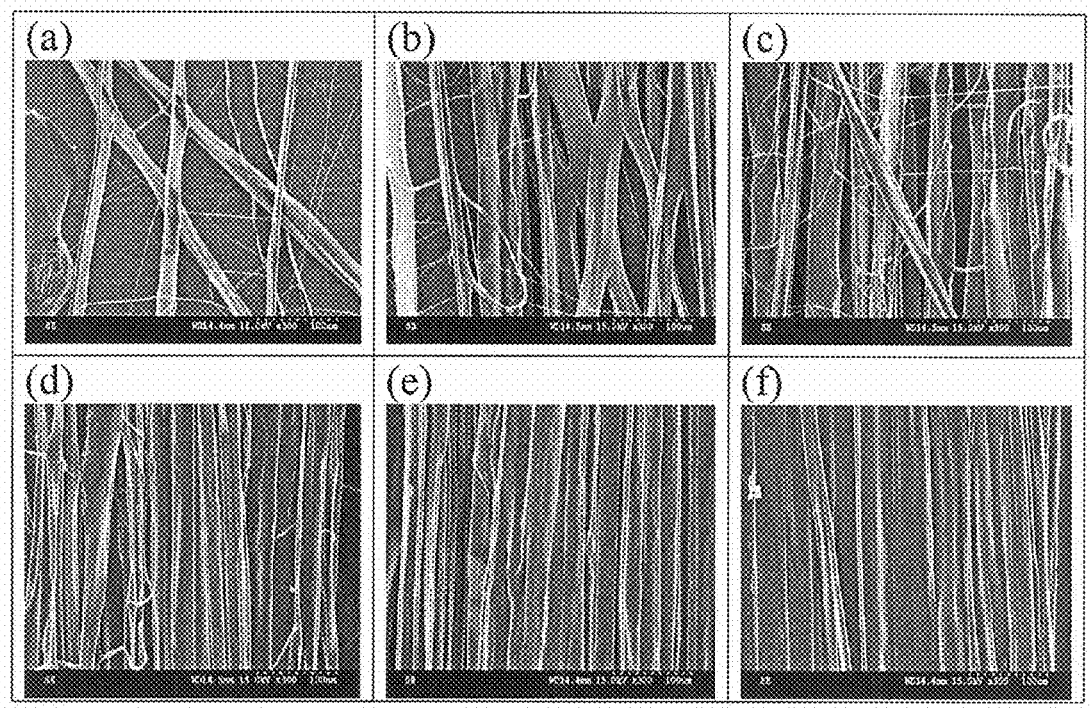
FIG. 18 shows the SEM images of PLLA hollow fibrous membranes prepared from different $FRR_{(i/o)}$: (a) 1 (b) 1.4 (c) 1.8 (d) 2.0 (e) 2.2 and (f) 2.4, at magnifications of 300×. Samples were collected in a 20-second period.
Figure 19:
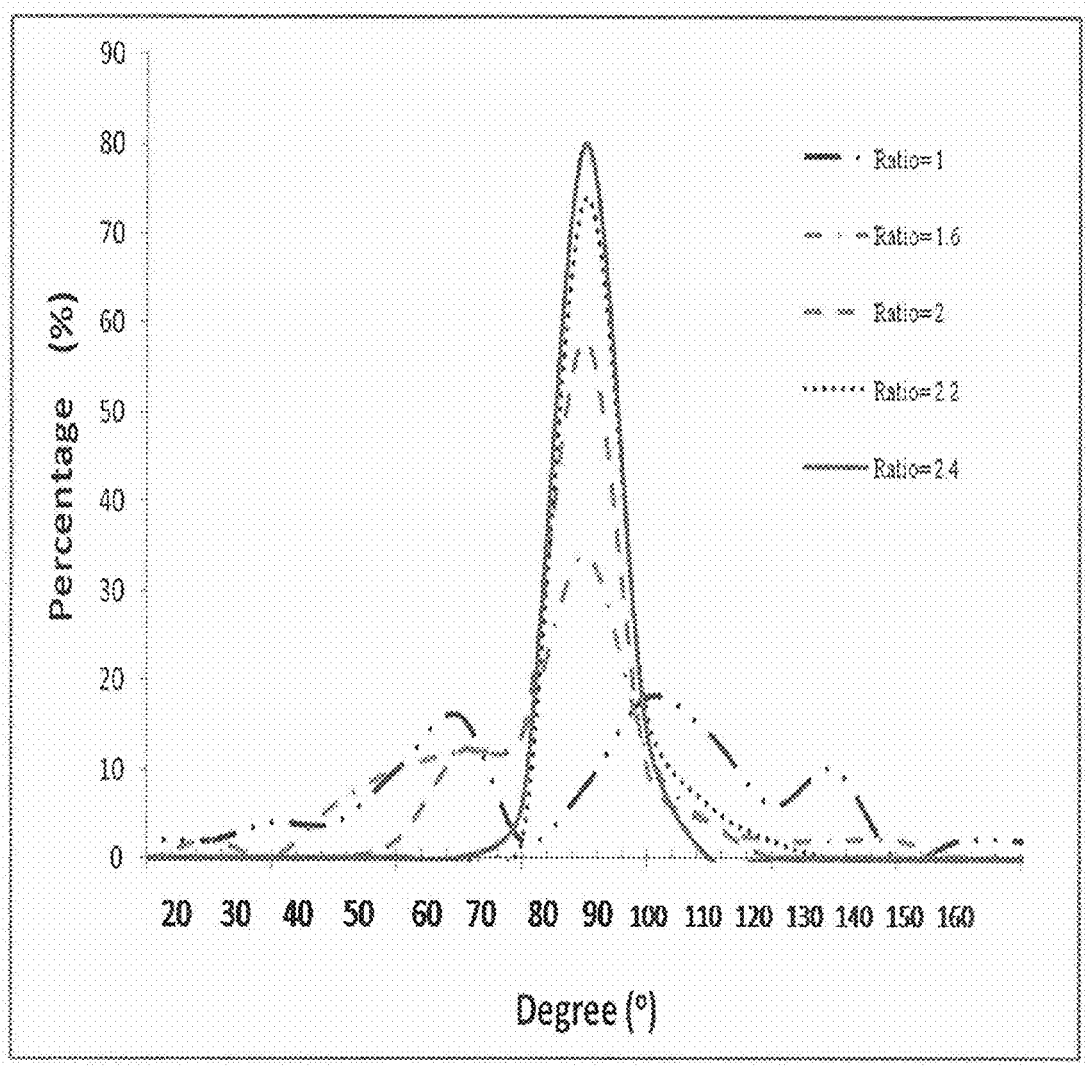
FIG. 19 shows the fiber alignment of PLLA hollow fibrous membranes prepared from different flow rate ratio (in/out).

Preparation of Fiber Assembly of the Invention Using Polymeric Solutions of Various Flow Rates The materials and methods were similar to those of Example 1 with only the flow rate of the inner solution was changed. By using an 8 w/v % PLLA solution as shell material and delivering it at a constant flow rate of 5 ml/hr, the inner flow rates of PEO solution were increased from 5 ml/hr to 12 ml/hr. It was observed that the collected fibers assembly scattered around the surface of the collecting drum when the flow rate ratio was low, i.e. 1 ml/hr to 1.6 ml/hr. At higher flow rate ratio, 1.8 ml/hr to 2.0 ml/hr, these fibers began to concentrate to a very narrow point and finally stood up when flow rate ratio reached 2.2 and 2.4, as shown in FIG. 17. With the increase in inner flow rate, the fibers also exhibited better alignment and tighter packing, as shown in FIG. 18, which provides the SEM images of PLLA hollow fibrous membranes prepared from different flow rate ratios: (a) 1.2 ml/hr, (b) 1.6 ml/hr (c) 2.0 ml/hr and (d) 2.4 ml/hr. As shown in FIG. 19, the PLLA electrospun hollow fiber assembly has the highest alignment with flow rate ratio of 2.4 ml/hr.

Example 7

Figure 20:
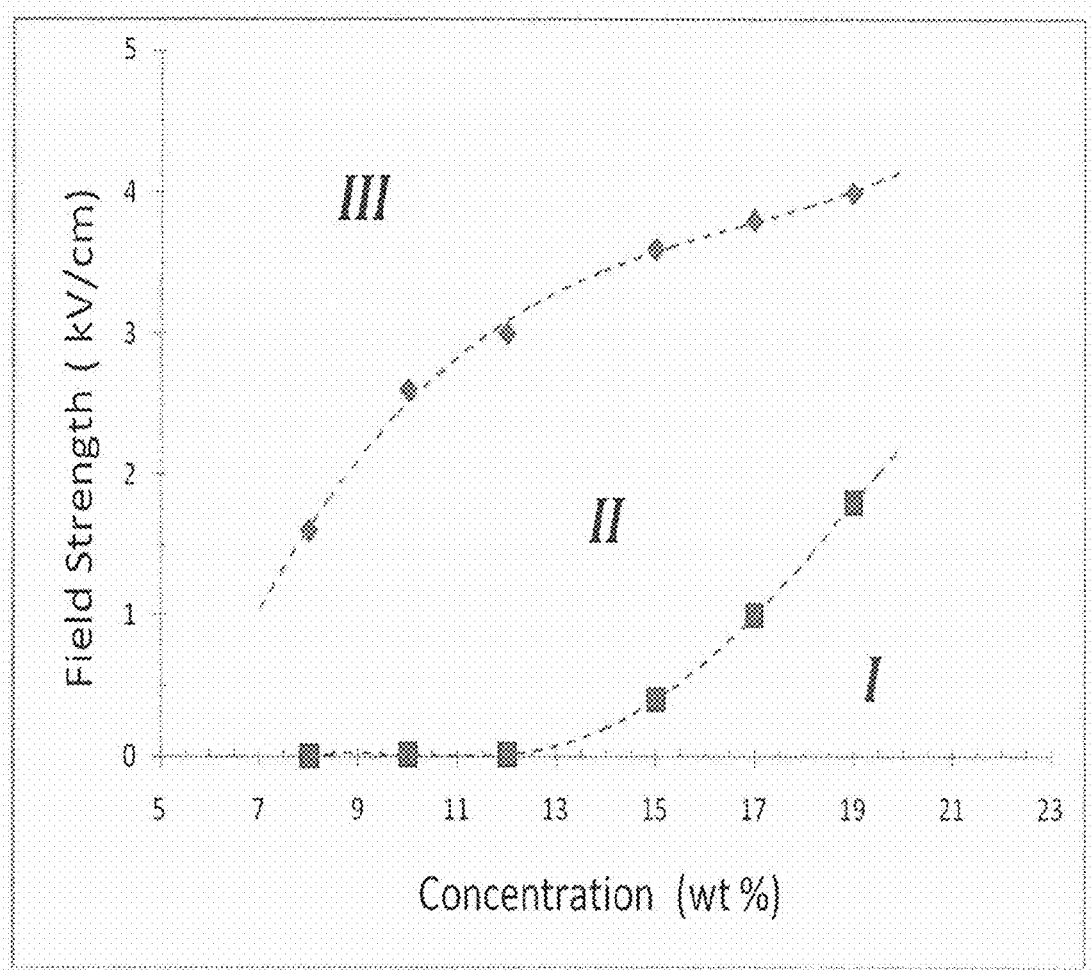
FIG. 20 shows an operational map focusing factors of applied voltage and weight of the spun fibers.
Figure 21:
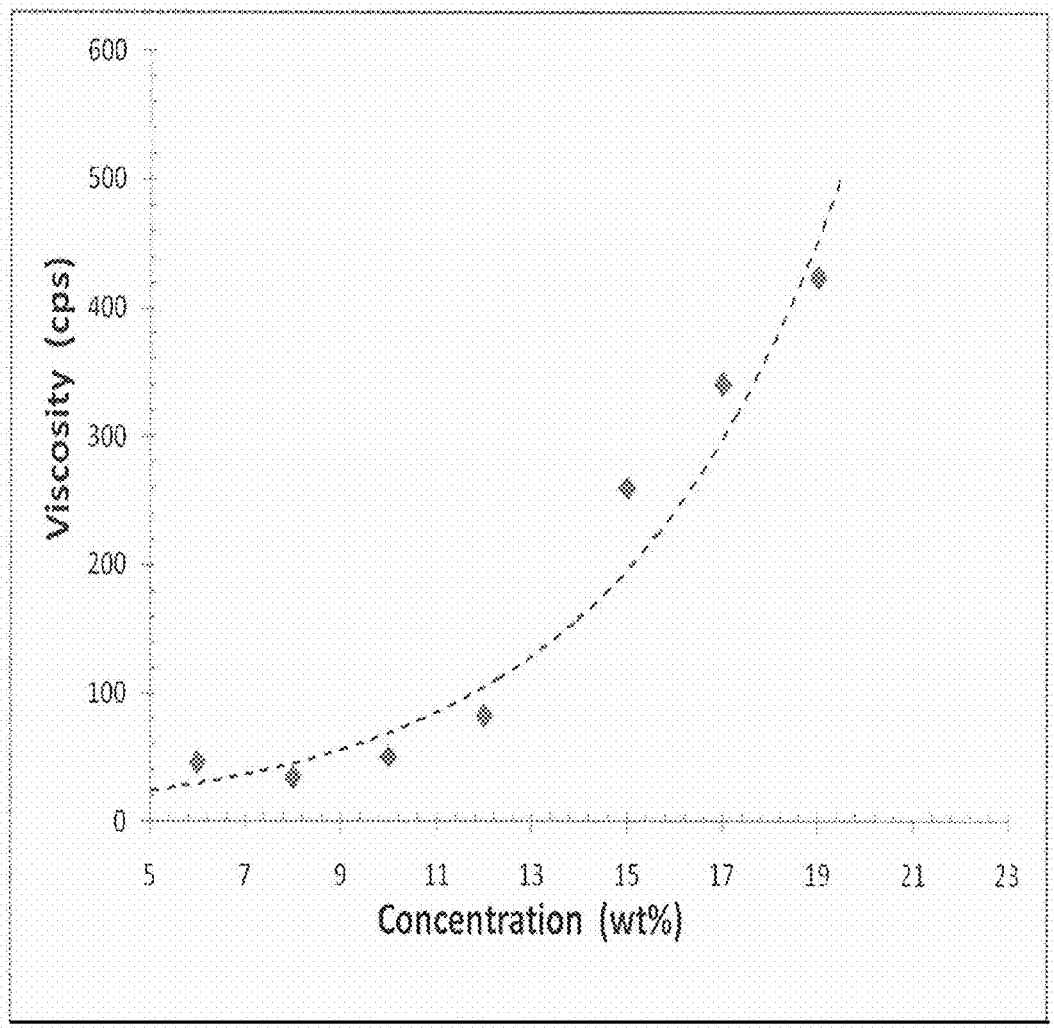
FIG. 21 shows the relationship between concentration of polymeric solution and viscosity if the solution.

Preparation of Fiber Assembly of the Invention Using Polymeric Solutions of Various Flow Rates in Combination with Various Voltages FIG. 20 provides an operational map focusing factors of applied voltage and weight of the spun fibers. A series of solutions with different PLLA concentrations, 8, 10, 12, 15, 17 and 19 wt %, were subjected to the increasing of the field strength from 0 to 4 kV/cm. The field strength where the fiber was begun to be pulled from the Taylor cone was recorded as the lower critical limit. While the field strength was too high for the leading a breakdown of the fiber or causing the dramatic swing, was marked as the upper field strength limit. This figure shows the three regions separated by the upper and lower voltage limits, see FIG. 20. An example spinning condition was described below. Under a spinning condition of 15 wt % PLLA solutions and voltage of 15 kV, as voltage increased, the spun fiber begin to pull from Taylor cone right of the spinneret, when the voltage reached a critical value, the fiber will be jetted toward the ground. At first, the flying fiber move toward the ground target. At the beginning, in region I, the solution viscosity is large enough preventing the solution being pulled by smaller electrostatic force. As the voltage increased and reached a critical value, these fibers were formed continuously and fly towards the ground target in region II. With the guiding of the electrical force and remaining weight of the fiber, the packing of these fibers and the growth of the stand-up membrane became possible. However, as the voltage continuously increased, region III, the electrical force become a dominating force causing the swing of the fiber, sometimes, the randomly spreading of the main jetted solution. As indicated by FIG. 21, the lower critical voltage for the formation of the membrane, was also in the same trend as those of the solution viscosity. It was noted that the formation of the early stage fiber was quite easily accomplished from the spinneret, such as 8 to 12 wt %, however, the excellent packing was only possible with some electrostatic applied, even at very low voltage. This operation map provides a useful guide as to produce the highly aligned and packed membrane.

Example 8

Cell Viability Assay

A primary molar tooth was obtained from the Center of Taipei Medical Teeth Bank and Dental Stem Cell Technology. The dental pulp was extracted from the excised teeth, and mechanically minced and treated with 0.25% trypsin-EDTA (Invitrogen, Carlsbad, Calif.) at 37° C. for 15 min. The resulting mixture of dental pulp cells was triturated using a pipette. After treatment of the dissociated cells with an equal volume of 0.5 mg/mL trypsin inhibitor (Invitrogen) and 2000 U/mL deoxyribonuclease I (Sigma, St. Louis, Mo.) at 37° C. for 15 min, the dental pulp suspension was centrifuged at 1500 rpm for 5 min and the supernatant was discarded.

Figure 22:
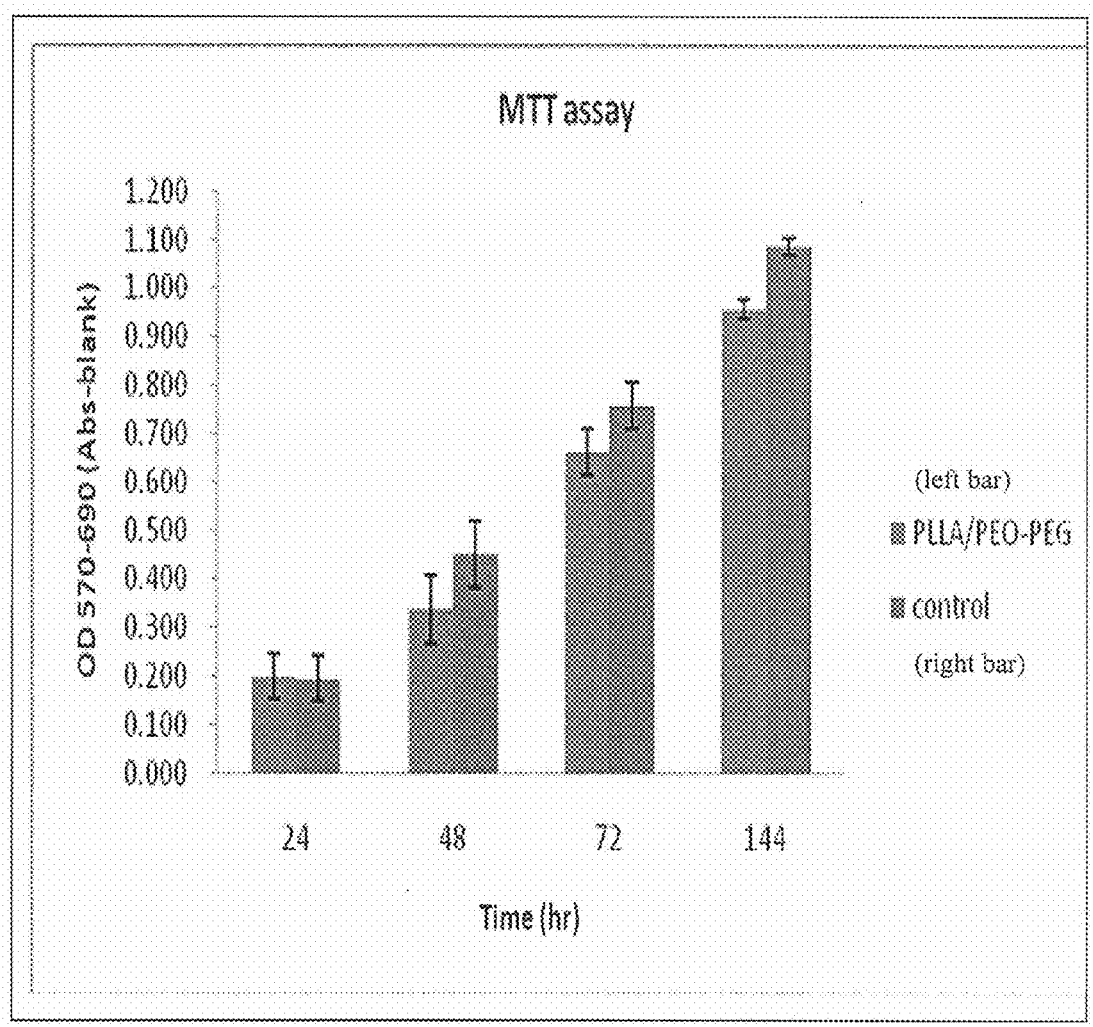
FIG. 22 shows cell viability of DPSCs in control group and PLLA group (n=9).

To test the biocompatibility of the PLLA electrospun hollow fibers assembly, the ISO 10993 standard procedure was followed (Sasaki, R., et al., Tubulation with dental pulp cells promotes facial nerve regeneration in rats. Tissue Engineering—Part A., 2008. 14(7): p. 1141-1147.), and the DPSCs were incubated in the PLLA scaffold for 6 days. The results showed that the cell viability was close to that of control group, suggesting that there was no cytotoxicity, as shown in FIG. 22.

What is claimed is:

1. A highly aligned and closely packed electrospun fiber assembly, wherein at least five (5) electrospun fibers are packed together to form a single layer and an orientation of the electro spun fibers is no greater than +/−5° relative to a longitudinal axis of the assembly, wherein the electrospun fibers are connected so that the electrospun fibers are aligned and closely packed to form the single layer, and wherein the alignment of the fibers is in the orientation no greater than +/−5°; wherein the fiber assembly is composed of a polymer selected from a group consisting of ethylene oxide, polyethylene oxide, ethylene glycol, polyethylene glycol, poly(lactic acid) (PLA), poly(glycolic acid) (PGA), poly(ethylene oxide) (PEO), nylon, polyesters, polyamides, poly(amino acids), polyimides, polyethers, polyketones, polyurethanes, polycaprolactones, polyacrylonitriles, polyaramides, conjugated polymers such as the electroluminescent polymer, poly(2-methoxy, 5 ethyl (2' hexyloxy) para-phenylene vinylene) (MEH-PPV), polyphenylenevinylenes, polyarylene-vinylenes, polythienolene-vinylenes, polypyrrolo-vinylenes, polyheteroarylene-vinylenes, polyanilines, polyphenylenes, polyarylenes, polythiophenes, polypyrroles, polyheteroarylenes, polyphenylene-ethynylenes, polyarylene-ethynylenes, polythieno-ethynylenes, polyheteroarylene-ethynylenes, and mixtures thereof; and
    wherein an average diameter of each fiber is about 15 to about 25 μm.

2. The fiber assembly of claim 1, wherein at least 20 fibers are packed together to form the single layer.

3. The fiber assembly of claim 1, wherein at least 50 fibers pack together to form the single layer.

4. The fiber assembly of claim 1, wherein the number of the fibers packed together in the fiber assembly ranges from 5 to 200.

5. The fiber assembly of claim 1, wherein the orientation of the fibers is no larger than +/−2°.

6. The fiber assembly of claim 1, wherein the orientation of the fibers is about +/−1° to about +/−5°.

7. The fiber assembly of claim 1, wherein the orientation of the fibers is about +/−1° to about +/−4°.

8. The fiber assembly of claim 1, wherein the fibers are hollow.

9. The fiber assembly of claim 1, wherein a length-to-diameter ratio (L/d) of each fiber is larger than about 20.

10. The fiber assembly of claim 1, wherein a L/d of each fiber is larger than about 100.

11. The fiber assembly of claim 1, wherein a L/d of each fiber is larger than about 1,000.

12. The fiber assembly of claim 1, wherein a L/d of each fiber is about 20 to about 10,000.

13. The fiber assembly of claim 1, wherein an average diameter of each fiber is about 20+/−2 μm.

14. The fiber assembly of claim 1, wherein an average wall thickness of the fibers is about 0.1 to about 10 μm.

15. The fiber assembly of claim 1, wherein an average wall thickness of each fiber is about 1 to about 5 μm.

16. The fiber assembly of claim 1, which can be used in medical tissue engineering and filtration unit.

17. The fiber assembly of claim 16, wherein the medical tissue engineering includes scaffold, nerve guide conduit and vascular tube.

18. The fiber assembly of claim 1, which can be in situ seeded with cells.

19. The fiber assembly of claim 18, wherein the cells are selected from a group consisting of nerve cells, epithelial cells, endothelial cells, fibroblasts, myoblasts, chondroblasts, osteoblasts, neural stem cells, Schwann cells, astrocytes, oligodendrocytes and their precursors, adrenal chromaffin cells, and the mixtures thereof.

* * * * *